United States Patent
Wu et al.

(10) Patent No.: US 6,488,930 B1
(45) Date of Patent: Dec. 3, 2002

(54) ANTI-CCR4 ANTIBODIES AND METHODS OF USE THEREFOR

(75) Inventors: Lijun Wu, Reading, MA (US); Nancy Ruffing, Somerville, MA (US); David Andrew, Waltham, MA (US)

(73) Assignee: Millennium Pharmaceuticals, Inc., Cambridge, MA (US)

(*) Notice: Subject to any disclaimer, the term of this patent is extended or adjusted under 35 U.S.C. 154(b) by 0 days.

(21) Appl. No.: 09/231,759

(22) Filed: Jan. 15, 1999

(51) Int. Cl.[7] .................. A61K 39/395; C07K 16/28
(52) U.S. Cl. ........................... 424/143.1; 530/388.2
(58) Field of Search .............. 530/388.22; 424/143.1

(56) References Cited

U.S. PATENT DOCUMENTS

| | | | |
|---|---|---|---|
| 5,440,021 A | 8/1995 | Chuntlarapai et al. | 530/388.22 |
| 5,543,503 A | 8/1996 | Chuntlarapai et al. | 530/388.22 |
| 5,919,776 A | 7/1999 | Hagmann et al. | 514/159 |
| 5,932,703 A | 8/1999 | Godiska et al. | 530/351 |
| 6,084,075 A | 7/2000 | Lind et al. | 530/388.22 |
| 6,150,132 A | 11/2000 | Wells et al. | 435/69.1 |
| 6,245,332 B1 | 6/2001 | Butcher et al. | 424/184.1 |

FOREIGN PATENT DOCUMENTS

| | | |
|---|---|---|
| EP | 0 860 446 A1 | 8/1998 |
| JP | 11-243960 | 9/1999 |
| WO | WO 95/08576 | 3/1995 |
| WO | WO 96/23068 | 8/1996 |
| WO | WO 98/27815 | 7/1998 |
| WO | WO98/44953 | 10/1998 |
| WO | WO 99/15666 | 4/1999 |

OTHER PUBLICATIONS

Chuntharapai et al. "Generation of Monoclonal Antibodies to Chemokine Receptors". Methods in Enzymology 288:15–27, 1997.*

Meyer, A., et al., "Cloning and Characterization of a Novel Murine Macrophage Inflammatory Protein–1α Receptor", *The Journal of Biological Chemistry*, 271(24):14445–14451 (1996).

Imai, T., et al., "Macrophage–Derived Chemokine Is a Functional Ligand for the CC Chemokine Receptor 4", *The Journal of Biological Chemistry*, 273(3):1764–1768 (1998).

Imai, T., et al., "The T Cell–Directed CC Chemokine TARC Is a Highly Specific Biological Ligand for CC Chemokine Receptor 4", *The Journal of Biological Chemistry*, 272(23):15036–15042 (1997).

Bonecchi, R., et al., "Differential Expression of Chemokine Receptors and Chemotactic Responsiveness of Type 1 T Helper Cells (Th1s) and Th2s", *J. Exp. Med.*, 187(1):129–134 (1998).

Dürig, J., et al., "Expression of Macrophage Inflammatory Protein–1α Receptors in Human CD34+ Hematopoietic Cells and Their Modulation by Tumor Necrosis Factor–α and Interferon–γ", *Blood*, 92(9):3073–3081 (1998).

Catalog of Santa Cruz Biotechnology, Inc., Research Antibodies 97/98, pp. 319–320 (1997).

Power, C.A., et al., "Molecular Cloning and Functional Expression of a Novel CC Chemokine Receptor cDNA from a Human Basophilic Cell Line", *J. Biol. Chem.*, 270(33):19495–19500 (1995).

Youn, B–S., et al., "Molecular Cloning and Characterization of a cDNA, CHEMR1, Endocing a Chemokine Receptor With a Homology to the Human C–C Chemokine Receptor, CCR–4", *Blood*, 89(12):4448–4460 (1997).

Genebank Accession No. X94151, Locus MMMIP1A2, "M. Musculus mRNA for MIP–1 Alpha Receptor 2" (1996).

Genebank Accession No. X85740, Locus HSCCCR3, "*H. sapiens* mRNA for C–C Chemokine Receptor–4" (1996).

Andrew, et al., "STCP–1 (MDC) CC Chemokine Acts Specifically on Chronically Activated Th2 Lymphocytes and Is Produced by Monocytes on Stimulation with Th2 Cytokines IL–4 and IL–13", *The Journal of Immunology*, 161:5027–5038 (1998).

Sallusto, et al., "Flexible Programs of Chemokine Receptor Expression on Human Polarized T Helper 1 and 2 Lymphocytes", *J. Exp. Med.*,187 (6): 875–883 (1998).

Förster et al., "A general method for screening mAbs specific for G–protein coupled receptors as exemplified by using epitope tagged BLR1–transfected 293 cells and solid–phase cell ELISA", *Biochemical and Biophysical Research Communications*, 196 (3): 1496–1503 (1993).

Ponath, P.D., "Chemokine receptor antagonists: novel therapeutics for inflammation and AIDS", *Exp. Opin. Invest. Drugs*, 7(1): 1–18 (1998).

Dürig, J., et al., "Expression of Macrophage Inflammatory Protein–1α Receptors in Human CD34+ Hematopoietic Cells and Their Modulation by Tumor Necrosis Factor–α and Interferon–γ", *Blood*, 92(9): 3073–3081 (1998).

Yoneyama, H., et al., "Pivotal Role of TARC, a CC Chemokine, in Bacteria–Induced Fulminant Hepatic Failure in Mice", *J. Clin. Invest.*, 102(11): 1933–1941 (1998).

(List continued on next page.)

Primary Examiner—John Ulm
(74) Attorney, Agent, or Firm—Hamilton, Brook, Smith & Reynolds, P.C.

(57) ABSTRACT

The present invention relates to an antibody or functional fragment thereof which binds to a mammalian (e.g., human) CC-chemokine receptor 4 (CCR4) or a portion of the receptor and blocks binding of a ligand to the receptor. The invention further relates to a method of inhibiting the interaction of a cell bearing mammalian CCR4 with a ligand thereof, and to use of the antibodies and fragments in research, therapeutic, prophylactic and diagnostic methods.

64 Claims, 17 Drawing Sheets

OTHER PUBLICATIONS

Wu, L., et al., "Interaction of Chemokine Receptor CCR5 with its Ligands: Multiple Domains for HIV–1 gp120 Binding and a Single Domain for Chemokine Binding", *J. Exp. Med.*, 186(8): 1373–1381 (1997).

Heath, H., et al., "Chemokine Receptor Usage by Human Eosinophils–The Importance of CCR3 Demonstrated Using an Antagonistic Monoclonal Antibody", *J. Clin. Invest.*, 99(2) 178–184 (1997).

Campbell, J.J., et al., "The chemokine receptor CCR4 in vascular recognition by cutaneous but not intestinal memory T cells" Nature, 400: 776–780 (1999).

XP002138299, Abstract No. 1999–603709[52], (abstract of Japanese Patent No. JP11243960) (1999).

Frade, J., et al., "Characterization of the CCR2 Chemokine Receptor: Functional CCR2 Receptor Expression in B Cells", *J. of Immunology*, 159:5576–5584 (1997).

Wu, L., et al., "Discrete Steps in Binding and Signaling of Interleukin–8 with Its Receptor", *J. of Biological Chemistry*, 271(49): 31202–31209 (1996).

Wu, L., et al., "Interaction of Chemokine Receptor CCR5 with its Ligands: Multiple Domains for HIV–1 gp120 Binding and a Single Domain for Chemokine Binding", J. Exp. Med., 186(8): 1373–1381 (1997).

* cited by examiner

ANTI-CCR4 ANTIBODIES AND METHODS OF USE THEREFOR

BACKGROUND OF THE INVENTION

Over the last decade chemokines have emerged as key mediators of inflammation as a result of their numerous proinflammatory activities which affect virtually every leukocyte type. More recently, chemokines have been recognized as a critical component of basal leukocyte trafficking essential for normal immune surveillance and response, as well as for several other functions in hematopoiesis, angiogenesis, control of viral infection, and T cell differentiation (Baggiolini et al., *Ann. Rev. Immunol.* 15:675 (1997); Zou et al., *Nature* 393:595 (1998); Tachibana et al., *Nature* 393:591 (1998)). This diverse array of biological activities, including mediation of a range of pro-inflammatory effects on leukocytes, such as triggering of chemotaxis, degranulation, synthesis of lipid mediators, and integrin activation, together with their critical role in the initiation and maintenance inflammatory diseases, and the recent identification of certain chemokine receptors as co-receptors for HIV-1 entry, have made chemokines and chemokine receptors an attractive new set of therapeutic targets.

Members of the chemokine family are produced and secreted by many cell types in response to early inflammatory mediators such as IL-1β or TNFα. The chemokine superfamily comprises two main branches: the α-chemokines (or CXC chemokines) which are characterized by a single amino acid separating the first 2 cysteines, and the β-chemokines (CC chemokines), which contain two adjacent cysteines. The α-chemokine branch includes proteins such as IL-8, neutrophil activating peptide-2 (NAP-2), melanoma growth stimulatory activity (MGSA/gro or GROA), and ENA-78, each of which have attracting and activating effects predominantly on neutrophils. The members of the β-chemokine branch affect other cell types such as monocytes, lymphocytes, basophils, and eosinophils (Oppenheim, J. J. et al., *Annu. Rev. Immunol.,* 9:617–648 (1991); Baggiolini, M., et al., *Adv. Imunol.,* 55:97–179 (1994); Miller and Krangel, *Crit. Rev. Immunol.,* 12:17–46 (1992); Jose, P. J., et al., *J. Exp. Med.,* 179:881–118 (1994); Ponath, P. D., et al., *J. Clin. Invest.,* 97:604–612 (1996)), and include proteins such as monocyte chemotactic proteins 1–4 (MCP-1, MCP-2, MCP-3, and MCP-4), RANTES, macrophage inflammatory proteins (MIP-1α, MIP-1β), thymus and activation-regulated chemokine (TARC; Imai et al., *J. Biol. Chem.* 271:21514–21521 (1996)) and macrophage-derived chemokine (MDC; Godiska et al., *J. Exp. Med.* 185:1595–1604 (1997)).

Chemokines bind to 7 transmembrane spanning G protein-coupled receptors (Murphy, P. M., *Annu. Rev. Immunol.,* 12:593–633 (1994)). A number of β chemokine receptors (CCR1–CCR10) have been identified to date, and the search for additional chemokine receptors is the subject of active research (Baggiolini, *Nature* 392:565–568 (1998)). Chemokine receptor CCR4 was identified by Power et al. (*J. Biol. Chem.* 270:19495–19500 (1995); Genbank accession number X85740) and Meyer et al. (*J. Biol. Chem.* 271(24):14445–14451 (1996); Genbank accession number X94151). A murine homolog of human CCR4 has also been identified (Youn et al., *Blood* 89(12):4448–4460 (1997)). CCR4 was originally found to signal in response to MCP-1, MIP-1α, and RANTES but more recently has been shown to be specific for the chemokines TARC and MDC (Imai et al., *J. Biol. Chem.* 272(23):15036–15042 (1997); Imai et al., *J. Biol. Chem.* 273:1764–1768 (1998)).

The selective recruitment of leukocyte subsets to sites of inflammation and the ordered trafficking of leukocytes through the circulation, tissues, lymphatic system and secondary lymphoid organs is controlled in part by the differential expression of chemokine receptors on subsets of cells. Such expression patterns would seem to ensure that a functionally related group of leukocytes can coordinately respond to a specific set of chemokines induced by a given stimulus. For T cells, PCR or Northern blotting indicates that the known receptors for CC chemokines are expressed on subsets of T cells. Delineating exactly which subsets express particular receptors is an area of intense study, because chemokine receptor expression may explain the localization or migration of various cell types, such as TH1 or TH2 T cells or tissue homing subsets. It may also determine which T cells are infected with different strains of HIV-1. However, most leukocytes express several chemokine receptors, many with complex and promiscuous ligand interactions. This makes elucidating the normal immune function for a specific receptor on a given cell type and determining the relevance to initiation and progression of disease difficult, especially since specific antibodies are not available for many chemokine receptors.

SUMMARY OF THE INVENTION

The present invention relates to an antibody (immunoglobulin) or functional fragment thereof (e.g., an antigen-binding fragment) which binds to a mammalian CC-chemokine receptor 4 (also referred to as CCR4, CKR-4, TARC-receptor and MDC receptor) or portion of the receptor (anti-CCR4). In one embodiment, the antibody of the present invention or fragment thereof has specificity for human CCR4 or a portion thereof. In another embodiment, the antibody or fragment of the invention blocks binding of a ligand (e.g., TARC, MDC, MCP-1, MIP-1α, RANTES) to the receptor and inhibits function associated with binding of the ligand to the receptor (e.g., leukocyte trafficking). In a preferred embodiment, the ligand is TARC and/or MDC. For example, as described herein, antibodies and fragments thereof of the present invention which bind human CCR4 or a portion thereof, can block binding of a chemokine (e.g., TARC, MDC, MCP-1, MIP-1α, RANTES) to the receptor and inhibit function associated with binding of the chemokine to the receptor. In a preferred embodiment, the chemokine is TARC and/or MDC. In one embodiment, the antibody is monoclonal antibody (mAb) LS141-1G1 (1G1) or an antibody which can compete with 1G1 for binding to human CCR4 or a portion of human CCR4. In another embodiment, the antibody is monoclonal antibody (mAb) LS185-2B10 (2B10) or an antibody which can compete with 2B10 for binding to human CCR4 or a portion of human CCR4. Functional fragments of the foregoing antibodies are also envisioned.

The present invention also relates to an antibody or functional fragment thereof (e.g., an antigen-binding fragment) which binds to a mammalian CCR4 or portion of the receptor and provides increased fluorescent staining intensity of CCR4 or compositions comprising CCR4 relative to other anti-CCR4 antibodies. In one embodiment, the antibody is monoclonal antibody 1G1 or 2B10 or an antibody which can compete with 1G1 or 2B10 for binding to human CCR4 or a portion of human CCR4.

The present invention further relates to a method of inhibiting the interaction of a cell bearing mammalian (e.g., human, non-human primate or murine) CCR4 with a ligand thereof, comprising contacting the cell with an effective amount of an antibody or functional fragment thereof which binds to a mammalian CCR4 or a portion of CCR4. Suitable cells include granulocytes, leukocytes, such as monocytes, macrophages, basophils and eosinophils, mast cells, and lymphocytes including T cells (e.g., CD8+ cells, CD4+ cells, CD25+ cells, CD45RO+ cells) such as Th1 and Th2 cells, and other cells expressing CCR4, such as a recombinant cell expressing CCR4 or portion thereof (e.g., transfected cells). In a particular embodiment, the antibody is 1G1 or 2B10 or an antibody which can compete with 1G1 or 2B10 for binding to human CCR4 or a portion of human CCR4.

Another embodiment of the invention relates to a method of inhibiting the interaction of a cell bearing mammalian CCR4 with a chemokine, comprising contacting said cell with an effective amount of an antibody or functional fragment thereof which binds to CCR4 or a portion of said receptor. In one embodiment of the method, the antibody or functional fragment thereof is any one or more of 1G1, 2B10, an antigen-binding fragment of 1G1 or 2B10, or an antibody or fragment thereof having an epitopic specificity which is the same as or similar to that of 1G1 or 2B10. Furthermore, the invention relates to a method of inhibiting a function associated with binding of a chemokine to CCR4, comprising administering an effective amount of an antibody or functional fragment thereof which binds to mammalian CCR4 or a portion of said receptor. In one aspect of the method, the antibody or functional fragment thereof is any one or more of 1G1, 2B10, an antigen-binding fragment of 1G1 or 2B10, or an antibody or fragment thereof having an epitopic specificity which is the same as or similar to that of 1G1 or 2B10.

Another aspect of the invention is a method of identifying expression of a mammalian CCR4 or portion of the receptor by a cell. According to the method, a composition comprising a cell or fraction thereof (e.g., a membrane fraction) is contacted with an antibody or functional fragment thereof (e.g., 1G1 or 2B10) which binds to a mammalian CCR4 protein or portion of the receptor under conditions appropriate for binding of the antibody thereto, and the formation of a complex between said antibody or fragment and said protein or portion thereof is detected. Detection of the complex, directly or indirectly, indicates the presence of the receptor or portion thereof on the cell or fraction thereof. The present invention also relates to a kit for use in detecting the presence of CCR4 or a portion thereof in a biological sample, comprising an antibody or functional fragment thereof which binds to a mammalian CCR4 or a portion of said receptor, and one or more ancillary reagents suitable for detecting the presence of a complex between said antibody or fragment and said protein or portion thereof.

Also encompassed by the present invention are methods of identifying additional ligands or other substances which bind a mammalian CCR4 protein, including inhibitors and/or promoters of mammalian CCR4 function. For example, agents having the same or a similar binding specificity as that of an antibody of the present invention or functional fragment thereof can be identified by a competition assay with said antibody or fragment. Thus, the present invention also encompasses methods of identifying ligands or other substances which bind the CCR4 receptor, including inhibitors (e.g., antagonists) or promoters (e.g., agonists) of receptor function. In one embodiment, cells which naturally express CCR4 receptor protein or suitable host cells which have been engineered to express a CCR4 receptor or variant encoded by a nucleic acid introduced into said cells are used in an assay to identify and assess the efficacy of ligands, inhibitors or promoters of receptor function. Such cells are also useful in assessing the function of the expressed receptor protein or polypeptide.

Thus, the invention also relates to a method of detecting or identifying an agent which binds a mammalian CCR4 or ligand binding variant thereof, comprising combining an agent to be tested, an antibody or antigen-binding fragment of the present invention (e.g., monoclonal antibody 1G1, monoclonal antibody 2B10, an antibody having an epitopic specificity which is the same as or similar to that of 1G1 or 2B10, antigen-binding fragments of 1G1 or 2B10) and a composition comprising a mammalian CCR4 protein or a ligand binding variant thereof. The foregoing components can be combined under conditions suitable for binding of the antibody or antigen-binding fragment to mammalian CCR4 protein or a ligand binding variant thereof, and binding of the antibody or fragment to the mammalian CCR4 protein or ligand binding variant is detected or measured, either directly or indirectly, according to methods described herein or other suitable methods. A decrease in the amount of complex formed relative to a suitable control (e.g., in the absence of the agent to be tested) is indicative that the agent binds said receptor or variant. The composition comprising a mammalian CCR4 protein or a ligand binding variant thereof can be a membrane fraction of a cell bearing recombinant CCR4 protein or ligand binding variant thereof. The antibody or fragment thereof can be labeled with a label such as a radioisotope, spin label, antigen label, enzyme label, fluorescent group and chemiluminescent group. These and similar assays can be used to detect agents, including ligands (e.g., chemokines which interact with CCR4) or other substances, including inhibitors or promoters of receptor function, which can bind CCR4 and compete with the antibodies described herein for binding to the receptor.

According to the present invention, ligands, inhibitors or promoters of receptor function can be identified in a suitable assay, and further assessed for therapeutic effect. Inhibitors of receptor function can be used to inhibit (reduce or prevent) receptor activity, and ligands and/or promoters can be used to induce (trigger or enhance) normal receptor function where indicated. The present invention also provides a method of treating inflammatory diseases, autoimmune diseases, atherosclerosis, and graft rejection, or HIV infection, comprising administering an inhibitor of receptor function (e.g., chemokine binding or HIV binding) to an individual (e.g., a mammal, such as a human). The present invention further provides a method of stimulating receptor function by administering a novel ligand or promoter to an individual, providing a new approach to selective stimulation of leukocyte function, which is useful, for example, in the treatment of infectious diseases and cancer.

The present invention also encompasses a method of inhibiting leukocyte trafficking in a patient, comprising administering to the patient an effective amount of an antibody or functional fragment thereof which binds to a mammalian CCR4 or portion of said receptor and inhibits function associated with binding of a ligand to the receptor.

The present invention also relates to a method of inhibiting or treating CCR4-mediated disorders, such as inflammatory disorders, comprising administering to a patient an effective amount of an antibody or functional fragment thereof which binds to a mammalian CCR4 or portion of said receptor and inhibits CCR4-mediated function.

The present invention further relates to an antibody or fragment thereof as described herein (e.g., monoclonal antibody 1G1, monoclonal antibody 2B10, an antigen-binding fragment of 1G1 or 2B10, an antibody having an epitopic specificity which is the same as or similar to that of 1G1 or 2B10) for use in therapy (including prophylaxis) or diagnosis, and to the use of such an antibody or fragment for the manufacture of a medicament for the treatment of a CCR4-mediated disorder, or other disease or inflammatory condition as described herein.

BRIEF DESCRIPTION OF THE DRAWINGS

In FIGS. 6A and 6B, a range of concentrations of chemokine was used, with 20 ug/ml of mAb 1G1 and MOPC21. In FIGS. 6C and 6D, 5 nM chemokine was used with a range of 1G1 and MOPC21 concentrations. The number of migrated cells was counted by flow cytometry using forward and side scatter.

DETAILED DESCRIPTION OF THE INVENTION

Figure 1:
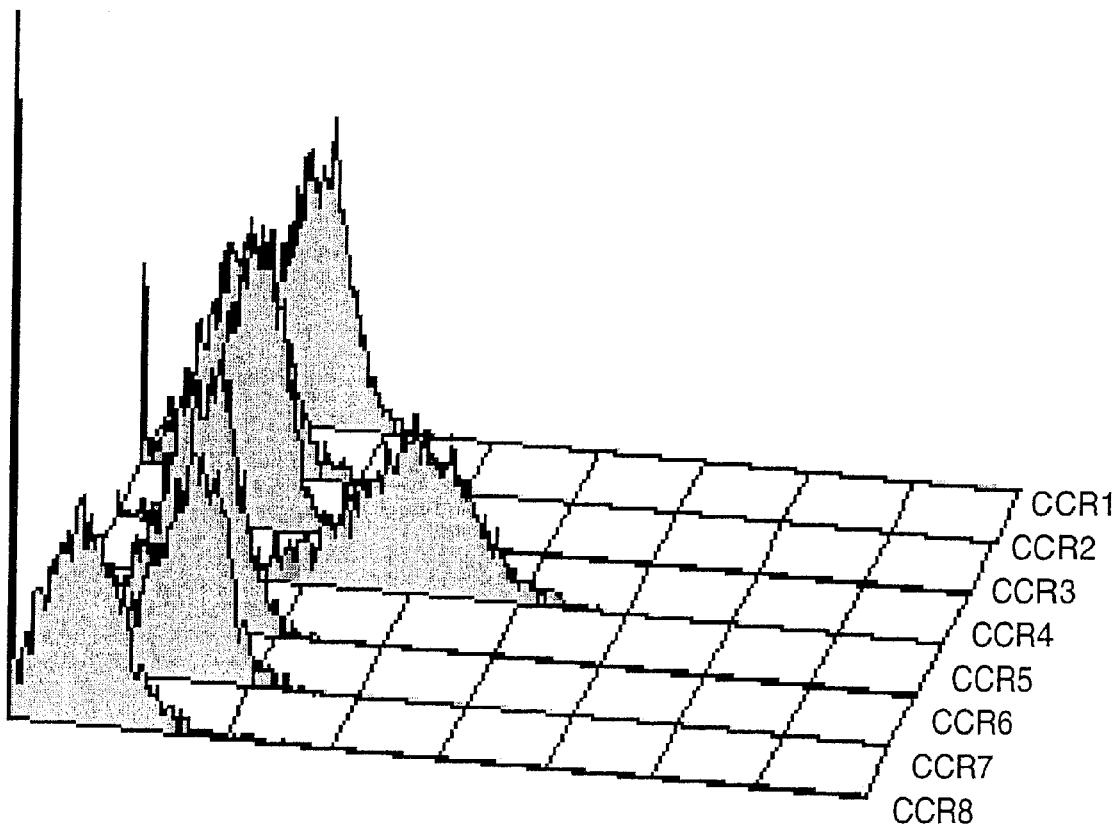
FIG. 1 is a FACScan® profile showing mAb 1G1 staining of various L1.2 transfectants. Stable L1.2 transfectants expressing different chemokine receptors, CCR1–CCR8, were stained with anti-CCR4 mAb 1G1. Negative control staining for all the L1.2 transfectants resembled that of the CCR1/L1.2 cells.
Figure 2A:
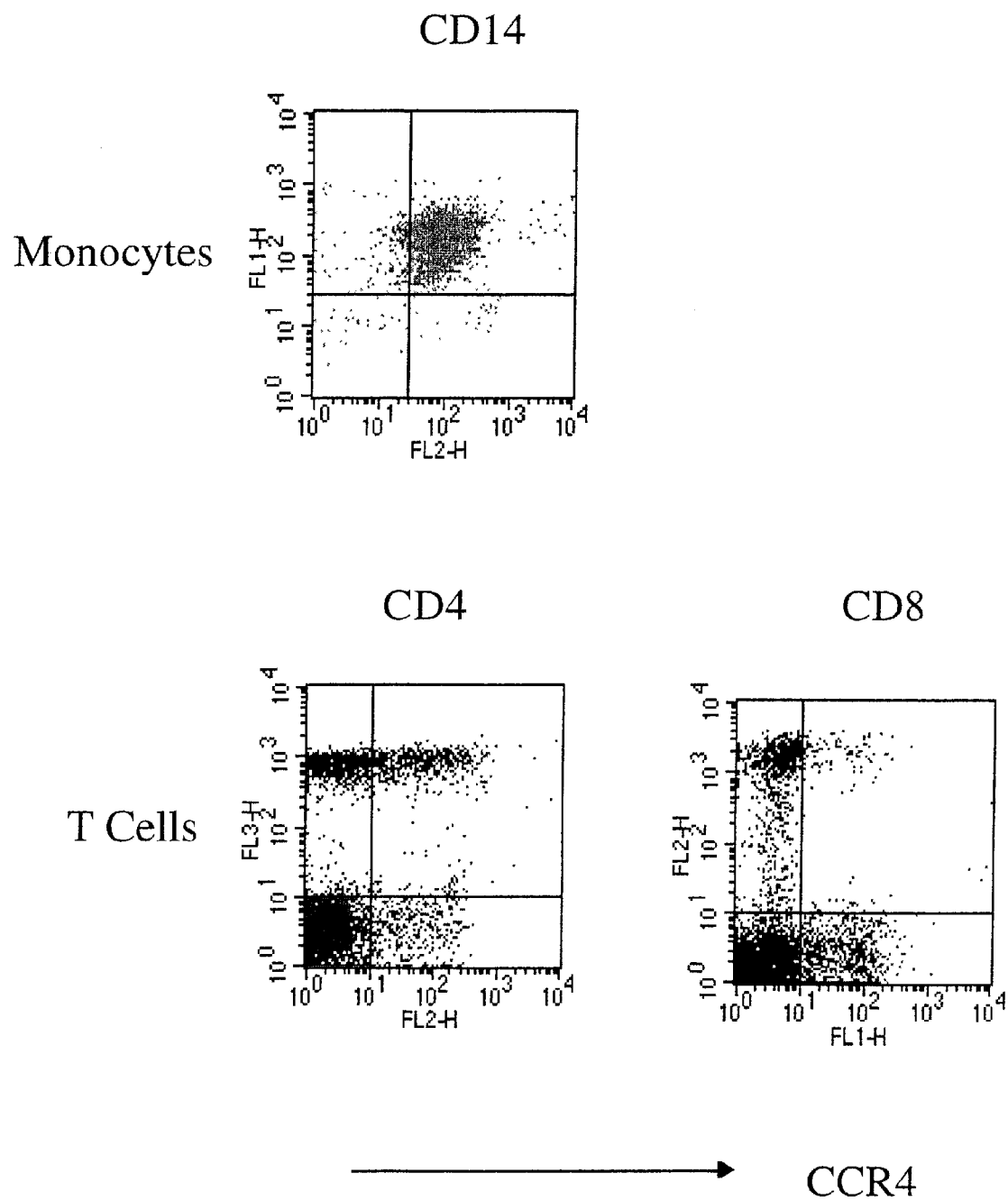
FIGS. 2A–2B are FACScan® dot plot showing CCR4 expression on various populations of peripheral blood lymphocytes. A two-color staining protocol was used to assess expression of CCR4 using mAb 1G1 (x-axis in all plots) and the cell markers (y-axis in all plots) CD14 (monocytes), CD4 and CD8 (T cells), CD16 and CD56 (NK cells) and CD19 and CD20 (B cells). The subset marker is indicated for each plot. Quadrants were set according to the staining of control mAbs. The staining was representative of multiple donors analyzed.
Figure 2B:
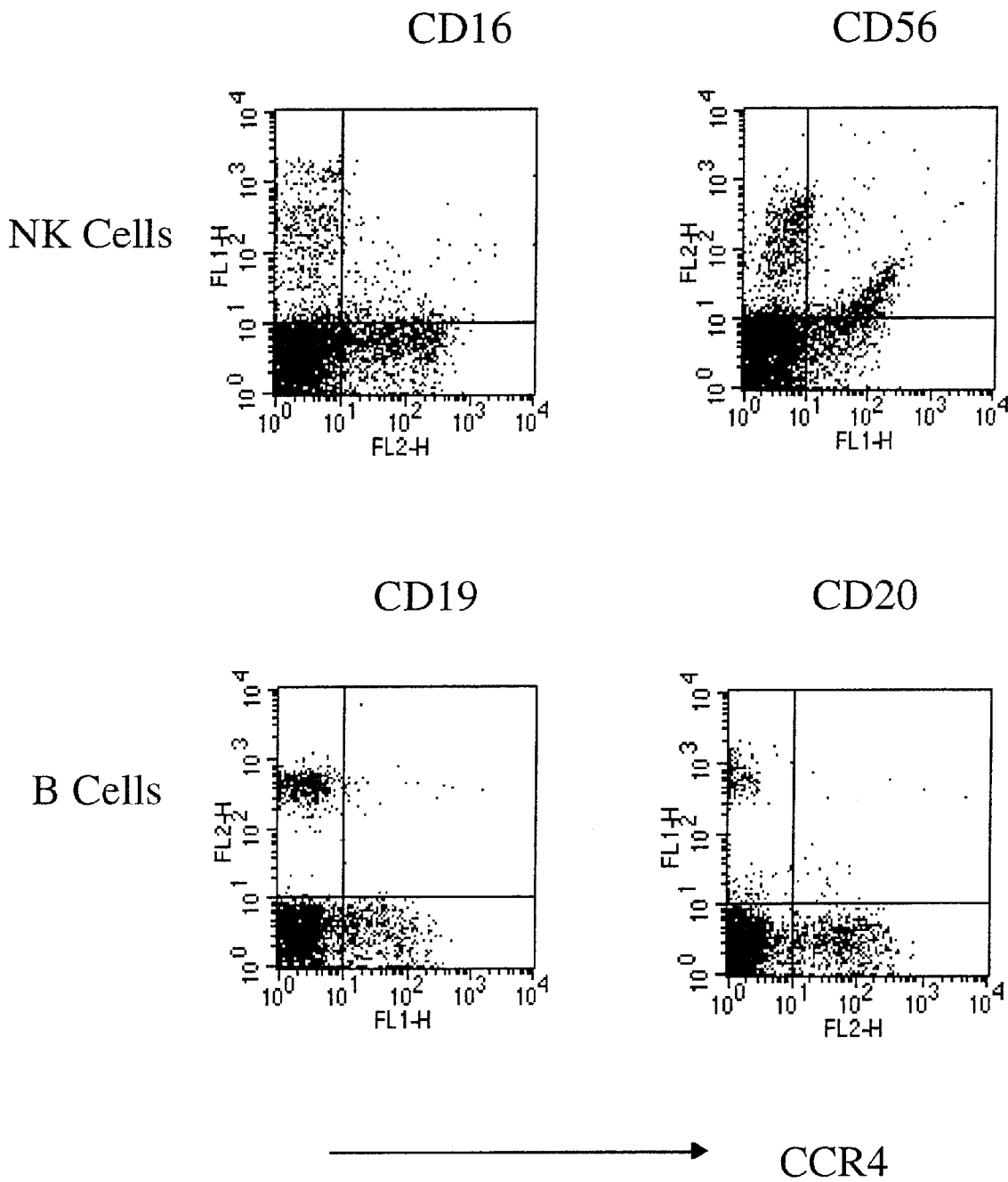
Figure 3A:
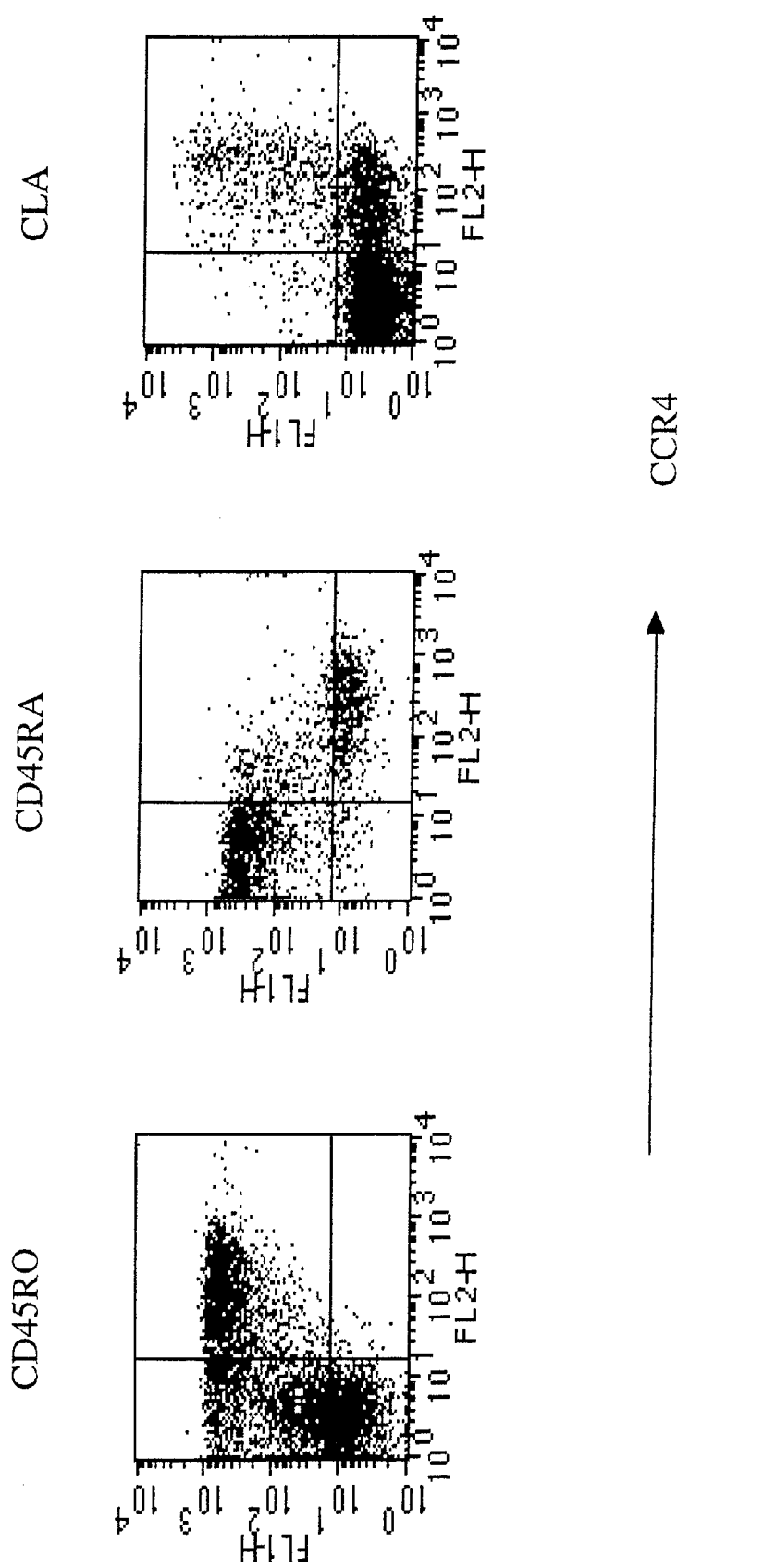
FIGS. 3A–3D are FACScan® dot plot showing CCR4 expression on CD4+ T cells. A three-color staining protocol was used to assess the expression of CCR4 (x-axis in all plots) and the T-cell subset markers (y-axis in all plots) on CD4+ T cells. The subset marker is indicated for each plot. Quadrants were set according to the staining of control mAbs. The staining was representative of multiple donors analyzed. The cells were analyzed by gating on CD4+ lymphocytes, and graphing CCR4 versus various cell markers. Quadrants were set according to the staining of control mAbs. Memory/naive markers: CD45RO, CD45RA; selectin/ligands: CLA, P-selectin ligand, E-selectin ligand, L selectin; integrins: ACT-1 ($\alpha 4\beta 7$), CD49d ($\alpha 4$), integrin $\beta 7$, CD29 ($\beta 1$), CD104 ($\beta 4$), and CD103 ($\alpha e$). CCR4 staining by mnAb 2B10 shows an identical pattern of staining.
Figure 3B:
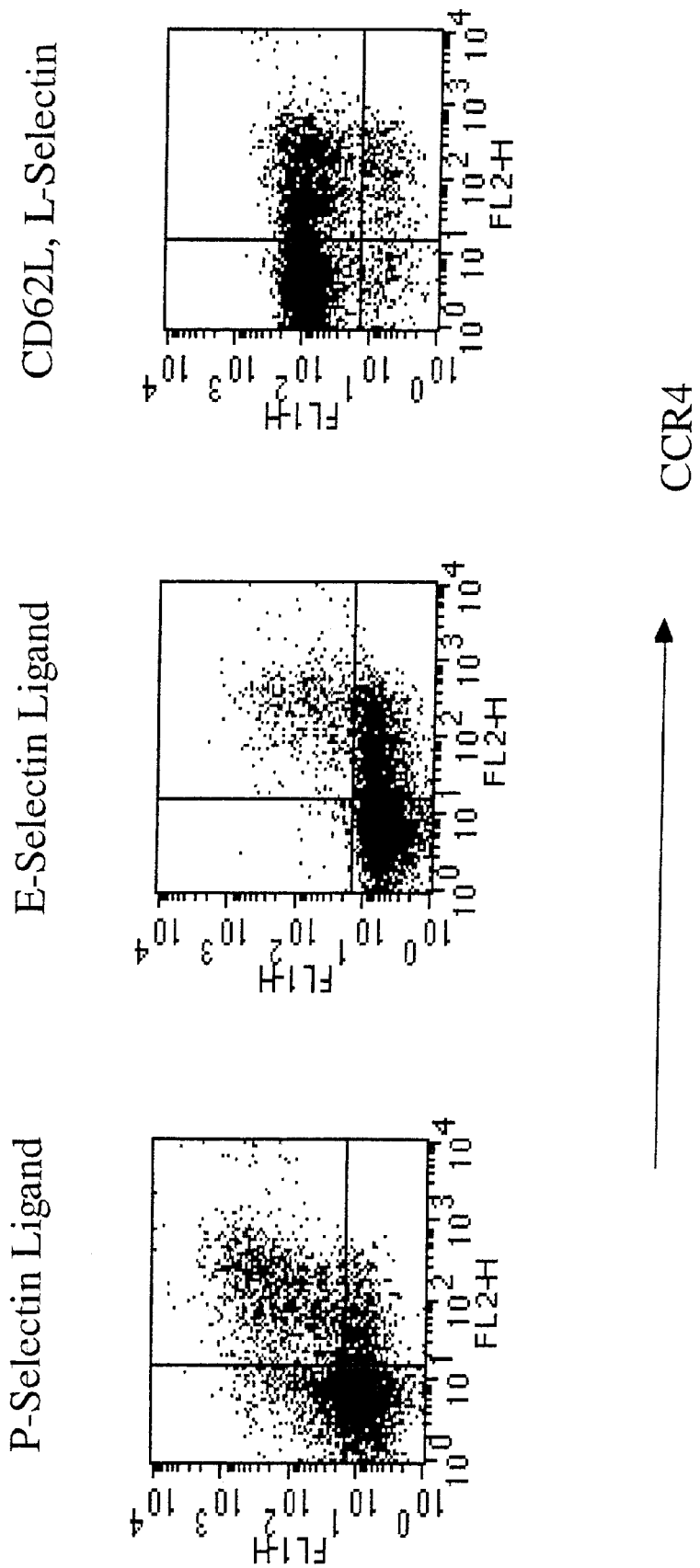
Figure 3C:
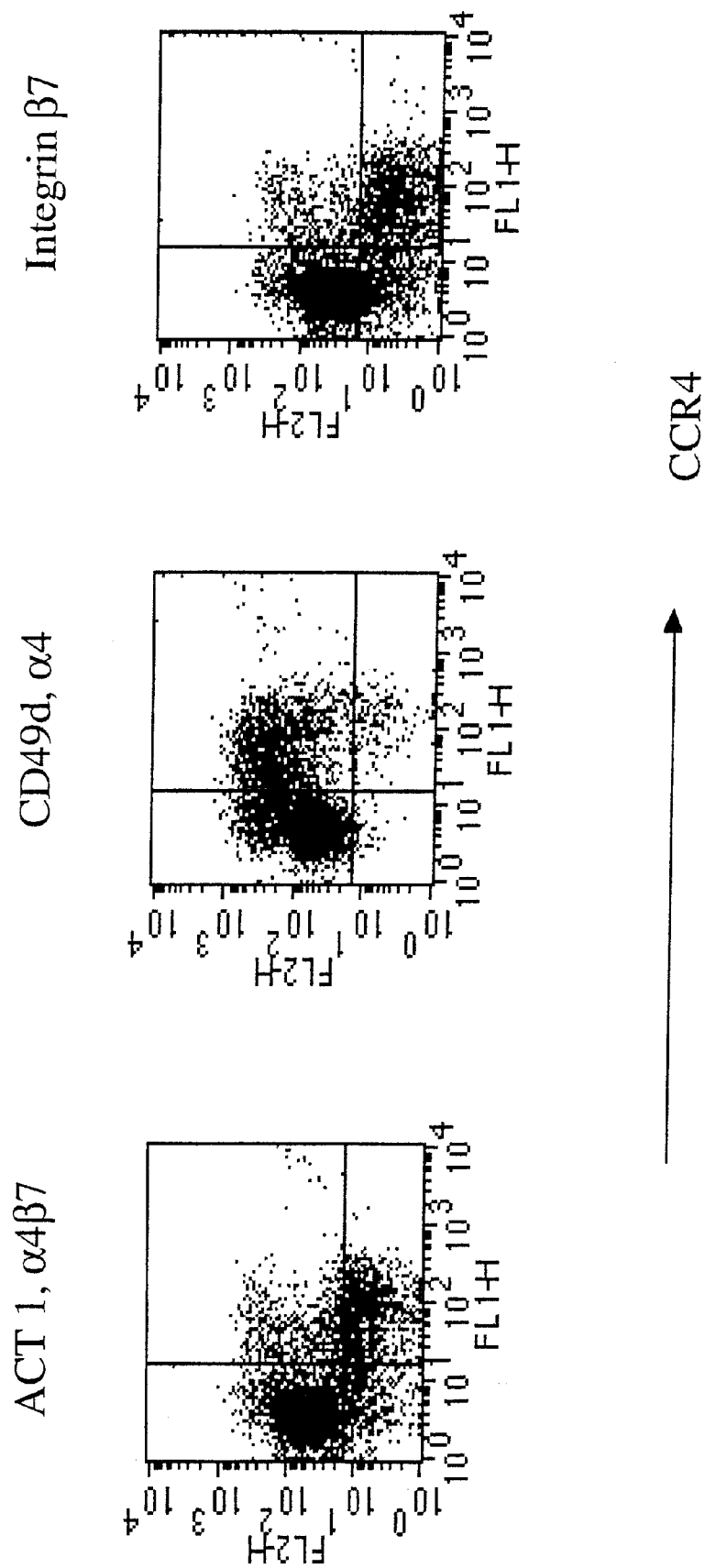
Figure 3D:
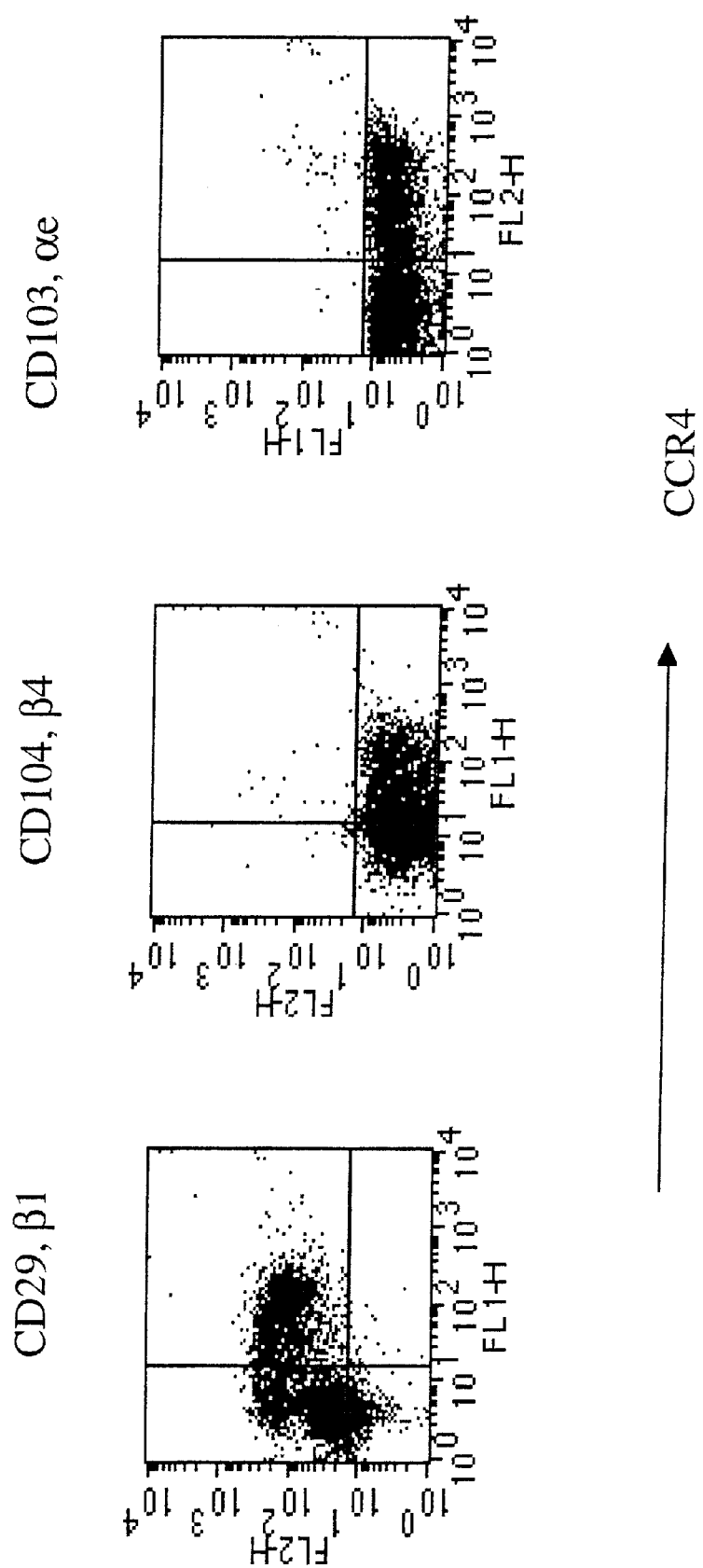

The present invention relates to an antibody (anti-CCR4) or functional fragment thereof which binds mammalian CC-chemokine receptor 4 (CCR4, CKR-4, TARC receptor or MDC receptor) or a portion of CCR4. In one embodiment, the antibody has specificity for human CCR4 or portion thereof. In one embodiment, the antibodies (immunoglobulins) are raised against an isolated and/or recombinant mammalian CCR4 or portion thereof (e.g., peptide) or against a host cell which expresses mammalian CCR4. In a preferred embodiment, the antibodies specifically bind human CCR4 receptor or a portion thereof, and in a particularly preferred embodiment the antibodies have specificity for a naturally occurring or endogenous human CCR4. Antibodies or functional fragments thereof which can inhibit one or more functions characteristic of a mammalian CCR4, such as a binding activity (e.g., ligand, inhibitor and/or promoter binding), a signaling activity (e.g., activation of a mammalian G protein, induction of a rapid and transient increase in the concentration of cytosolic free calcium $[Ca^{2+}]_i$), and/or stimulation of a cellular response (e.g., stimulation of chemotaxis, exocytosis or inflammatory mediator release by leukocytes, integrin activation) are also encompassed by the present invention, such as an antibody which can inhibit binding of a ligand (i.e., one or more ligands) to CCR4 and/or one or more functions mediated by CCR4 in response to a ligand. For example, in one aspect, the antibodies or functional fragments thereof can inhibit (reduce or prevent) the interaction of receptor with a natural ligand, such as MDC, TARC, MCP-1, MIP-1$\alpha$ or RANTES. In one embodiment, the ligand is TARC and/or MDC. In another aspect, an antibody or functional fragment thereof that binds to CCR4 can inhibit binding of TARC, MDC, MCP-1, MIP-1α, and/or RANTES to mammalian CCR4 (e.g., human CCR4, non-human primate CCR4, murine CCR4). The antibodies or functional fragments thereof of the present invention can inhibit functions mediated by human CCR4, including leukocyte trafficking, T cell activation, inflammatory mediator release and/or leukocyte degranulation. In a particular embodiment, antibodies or functional fragments thereof demonstrate inhibition of chemokine-induced (e.g., TARC- or MDC-induced) chemotaxis of cells, preferably at less than about 0.50 μg/ml, preferably less than about 0.30 μg/ml, and more preferably less than about 0.27 μg/ml.

In a further embodiment of the invention, the antibodies or functional fragments thereof of the invention can inhibit binding of a CCR4 ligand (e.g., a chemokine) to CCR4, preferably with an $IC_{50}$ of less than about 1.5 μg/ml. In another embodiment, the antibodies or functional fragments thereof of the invention can inhibit binding of a CCR4 ligand (e.g., a chemokine) to CCR4 with an $IC_{50}$ of less than about 1.5 ng/ml.

Murine monoclonal antibodies specific for CCR4, designated 1G1 and 2B10, were produced as described herein. In a preferred embodiment, the antibodies of the present invention bind human CCR4, and have an epitopic specificity which is the same as or similar to that of murine 1G1 or 2B10 antibody described herein. Antibodies with an epitopic specificity which is the same as or similar to that of murine 1G1 monoclonal antibody can be identified by their ability to compete with murine 1G1 monoclonal antibody for binding to human CCR4 (e.g., to cells bearing human CCR4, such as transfectants bearing CCR4, CD8+ cells, CD4+ cells, CDR45RO+ cells, CD25+ cells, monocytes, dendritic cells, macrophages and basophils). Similarly, antibodies with an epitopic specificity which is the same as or similar to that of murine 2B10 monoclonal antibody can be identified by their ability to compete with murine 2B10 monoclonal antibody for binding to human CCR4. Using receptor chimeras (Rucker et al., Cell 87:437–446 (1996)), the binding site (i.e., epitopic specificity) of mAbs 1G1 and 2B10 can be mapped. Using these or other suitable techniques, antibodies having an epitopic specificity which is the same as or similar to that of an antibody of the present invention can be identified.

The invention also relates to a bispecific antibody, or functional fragment thereof (e.g., $F(ab')_2$), which has the same or similar epitopic specificity as at least two of the antibodies described herein (see, e.g., U.S. Pat. No. 5,141,736 (Iwasa et al.), U.S. Pat. Nos. 4,444,878, 5,292,668, 5,523,210 (all to Paulus et al.) and U.S. Pat. No. 5,496,549 (Yamazaki et al.). For example, a bispecific antibody of the present invention can have the same or similar epitopic specificity as mAb 1G1 and 2B10.

Hybridoma cell lines producing antibodies according to the present invention were deposited on Jan. 6, 1999, on behalf of LeukoSite, Inc., 215 First Street, Cambridge, Mass. 02142, U.S.A., at the American Type Culture Collection, 10801 University Boulevard, Manassas, Va. 20110, U.S.A., under Accession Nos. HB-12624 (LS141-1G1-65-15-1 (1G1)) and HB-12625 (LS185-2B10-4-1). The present invention also pertains to the hybridoma cell lines deposited under ATCC Accession No. HB-12624 and ATCC Accession No. HB-12625, as well as to the monoclonal antibodies produced by the hybridoma cell lines deposited under ATCC Accession Nos. HB-12624 and HB-12625.

The antibodies of the present invention can be polyclonal or monoclonal, and the term "antibody" is intended to encompass both polyclonal and monoclonal antibodies. Furthermore, it is understood that methods described herein which utilize 1G1 can also utilize functional fragments (e.g., antigen-binding fragments) of 1G1, antibodies which have the same or similar epitopic specificity as 1G1, and combinations thereof, optionally in combination with antibodies or fragments having an epitopic specificity which is not the same as or similar to 1G1; similarly, methods described as utilizing 2B10 can also utilize functional fragments of 2B10, antibodies which have the same or similar epitopic specificity as 2B10, and combinations thereof, optionally in combination with antibodies or fragments having an epitopic specificity which is not the same as or similar to 2B10. Antibodies of the present invention can be raised against an appropriate immunogen, such as isolated and/or recombinant mammalian CCR4 protein or portion thereof, or synthetic molecules, such as synthetic peptides. In a preferred embodiment, cells which express receptor, such as transfected cells, can be used as immunogens or in a screen for antibody which binds receptor.

The antibodies of the present invention, and fragments thereof, are useful in therapeutic, diagnostic and research applications as described herein. The present invention encompasses an antibody or functional portion thereof of the present invention (e.g., mAb 1G1 or 2B10, or antigen-binding fragments thereof) for use in therapy (including prophylaxis) or diagnosis (e.g., of particular diseases or conditions as described herein), and use of such antibodies or functional portions thereof for the manufacture of a medicament for use in treatment of diseases or conditions as described herein.

Preparation of immunizing antigen, and polyclonal and monoclonal antibody production can be performed as described herein, or using other suitable techniques. A variety of methods have been described (see e.g., Kohler et al., Nature, 256: 495–497 (1975) and Eur. J. Immunol. 6: 511–519 (1976); Milstein et al., Nature 266: 550–552 (1977); Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); Current Protocols In Molecular Biology, Vol. 2 (Supplement 27, Summer '94), Ausubel, F. M. et al., Eds., (John Wiley & Sons: New York, N.Y.), Chapter 11, (1991)). Generally, a hybridoma can be produced by fusing a suitable immortal cell line (e.g., a myeloma cell line such as SP2/0) with antibody producing cells. The antibody producing cell, preferably from the spleen or lymph nodes, are obtained from animals immunized with the antigen of interest. The fused cells (hybridomas) can be isolated using selective culture conditions, and cloned by limiting dilution. Cells which produce antibodies with the desired binding properties can be selected by a suitable assay (e.g., ELISA).

Other suitable methods of producing or isolating antibodies which bind CCR4, including human or artificial antibodies, can be used, including, for example, methods which select recombinant antibody (e.g., single chain Fv or Fab) from a library, or which rely upon immunization of transgenic animals (e.g., mice) capable of producing a repertoire of human or artificial antibodies (see e.g., Jakobovits et al., Proc. Natl. Acad. Sci. USA, 90: 2551–2555 (1993); Jakobovits et al., Nature, 362: 255–258 (1993); Lonberg et al., U.S. Pat. No. 5,545,806; Surani et al., U.S. Pat. No. 5,545,807).

Single chain antibodies, and chimeric, humanized or primatized (CDR-grafted) antibodies, as well as chimeric or CDR-grafted single chain antibodies, and the like, comprising portions derived from different species, are also encompassed by the present invention and the term "antibody". The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; and Queen et al., U.S. Pat. Nos. 5,585,089, 5,698,761 and 5,698,762. See also, Newman, R. et al., *BioTechnology*, 10: 1455–1460 (1992), regarding primatized antibody, and Ladner et al., U.S. Pat. No. 4,946,778 and Bird, R. E. et al., *Science*, 242: 423–426 (1988)) regarding single chain antibodies.

In addition, functional fragments of antibodies, including fragments of chimeric, humanized, primatized or single chain antibodies, can also be produced. Functional fragments of the foregoing antibodies retain at least one binding function and/or modulation function of the full-length antibody from which they are derived. Preferred functional fragments retain an antigen-binding function of a corresponding full-length antibody (e.g., retain the ability to bind a mammalian CCR4). Particularly preferred functional fragments retain the ability to inhibit one or more functions characteristic of a mammalian CCR4, such as a binding activity, a signaling activity, and/or stimulation of a cellular response. For example, in one embodiment, a functional fragment can inhibit the interaction of CCR4 with one or more of its ligands (e.g., TARC, MDC, MCP-1, MIP-1$\alpha$, and/or RANTES), and/or can inhibit one or more receptor-mediated functions, such as leukocyte trafficking, HIV entry into cells, T cell activation, inflammatory mediator release and/or leukocyte degranulation.

For example, antibody fragments capable of binding to a mammalian CCR4 receptor or portion thereof, including, but not limited to, Fv, Fab, Fab' and F(ab')$_2$ fragments are encompassed by the invention. Such fragments can be produced by enzymatic cleavage or by recombinant techniques, for example. For instance, papain or pepsin cleavage can generate Fab or F(ab')$_2$ fragments, respectively. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the $CH_1$ domain and hinge region of the heavy chain.

The term "humanized immunoglobulin" as used herein refers to an immunoglobulin comprising portions of immunoglobulins of different origin, wherein at least one portion is of human origin. Accordingly, the present invention relates to a humanized immunoglobulin which binds mammalian CCR4 (e.g., human CCR4, murine CCR4), said immunoglobulin comprising an antigen-binding region of nonhuman origin (e.g., rodent) and at least a portion of an immunoglobulin of human origin (e.g., a human framework region, a human constant region or portion thereof). For example, the humanized antibody can comprise portions derived from an immunoglobulin of nonhuman origin with the requisite specificity, such as a mouse, and from immunoglobulin sequences of human origin (e.g., a chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin of the present invention is an immunoglobulin containing one or more immunoglobulin chains comprising a CDR of nonhuman origin (e.g., one or more CDRs derived from an antibody of nonhuman origin) and a framework region derived from a light and/or heavy chain of human origin (e.g., CDR-grafted antibodies with or without framework changes). In one embodiment, the humanized immunoglobulin can compete with murine 1G1 or 2B10 monoclonal antibody for binding to human CCR4. In a preferred embodiment, the antigen-binding region of the humanized immunoglobulin (a) is derived from 1G1 or 2B10 monoclonal antibody (e.g., as in a humanized immunoglobulin comprising CDR1, CDR2 and CDR3 of the 1G1 or 2B10 light chain and CDR1, CDR2 and CDR3 of the 1G1 or 2B10 heavy chain). Chimeric or CDR-grafted single chain antibodies are also encompassed by the term humanized immunoglobulin.

Such humanized immunoglobulins can be produced using synthetic and/or recombinant nucleic acids to prepare genes (e.g., cDNA) encoding the desired humanized chain. For example, nucleic acid (e.g., DNA) sequences coding for humanized variable regions can be constructed using PCR mutagenesis methods to alter DNA sequences encoding a human or humanized chain, such as a DNA template from a previously humanized variable region (see e.g., Kamman, M., et al., *Nucl. Acids Res.*, 17: 5404 (1989)); Sato, K., et al., *Cancer Research*, 53: 851–856 (1993); Daugherty, B. L. et al., *Nucleic Acids Res.*, 19(9): 2471–2476 (1991); and Lewis, A. P. and J. S. Crowe, *Gene*, 101: 297–302 (1991)). Using these or other suitable methods, variants can also be readily produced. In one embodiment, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993; Knappik et al., WO 97/08320, published Mar. 6, 1997)).

Anti-idiotypic antibodies are also provided. Anti-idiotypic antibodies recognize antigenic determinants associated with the antigen-binding site of another antibody. Anti-idiotypic antibodies can be prepared against second antibody by immunizing an animal of the same species, and preferably of the same strain, as the animal used to produce the second antibody. See e.g., U.S. Pat. No. 4,699,880.

The present invention also pertains to the hybridoma cell lines deposited under ATCC Accession Nos. HB 12624 and HB-12628, as well as to the monoclonal antibodies produced by the hybridoma cell lines deposited under ATCC Accession Nos. HB-12624 and HB-12625. The cell lines of the present invention have uses other than for the production of the monoclonal antibodies. For example, the cell lines of the present invention can be fused with other cells (such as suitably drug-marked human myeloma, mouse myeloma, human-mouse heteromyeloma or human lymphoblastoid cells) to produce additional hybridomas, and thus provide for the transfer of the genes encoding the monoclonal antibodies. In addition, the cell lines can be used as a source of nucleic acids encoding the anti-CCR4 immunoglobulin chains, which can be isolated and expressed (e.g., upon transfer to other cells using any suitable technique (see e.g., Cabilly et al., U.S. Pat. No. 4,816,567; Winter, U.S. Pat. No. 5,225,539)). For instance, clones comprising a rearranged anti-CCR4 light or heavy chain can be isolated (e.g., by PCR) or cDNA libraries can be prepared from mRNA isolated from the cell lines, and cDNA clones encoding an anti-CCR4 immunoglobulin chain can be isolated. Thus, nucleic acids encoding the heavy and/or light chains of the antibodies or portions thereof can be obtained and used in accordance with recombinant DNA techniques for the production of the specific immunoglobulin, immunoglobulin chain, or variants thereof (e.g., humanized immunoglobulins) in a variety of host cells or in an in vitro translation system. For example, the nucleic acids, including cDNAs, or derivatives thereof encoding variants such as a humanized immunoglobulin or immunoglobulin chain, can be placed into suitable prokaryotic or eukaryotic vectors (e.g., expression vectors) and introduced into a suitable host cell by an appropriate method (e.g., transformation, transfection, electroporation, infection), such that the nucleic acid is operably linked to one or more expression control elements (e.g., in the vector or integrated into the host cell genome). For production, host cells can be maintained under conditions suitable for expression (e.g., in the presence of inducer, suitable media supplemented with appropriate salts, growth factors, antibiotic, nutritional supplements, etc.), whereby the encoded polypeptide is produced. If desired, the encoded protein can be recovered and/or isolated (e.g., from the host cells, medium, milk). It will be appreciated that the method of production encompasses expression in a host cell of a transgenic animal (see e.g., WO 92/03918, GenPharm International, published Mar. 19, 1992).

As described herein, antibodies and functional fragments thereof of the present invention can block (inhibit) binding of a ligand to CCR4 and/or inhibit function associated with binding of the ligand to the CCR4. As discussed below various methods can be used to assess inhibition of binding of a ligand to CCR4 and/or function associated with binding of the ligand to the receptor.

Binding Assays

As used herein "mammalian CCR4" refers to naturally occurring or endogenous mammalian CCR4 proteins and to proteins having an amino acid sequence which is the same as that of a naturally occurring or endogenous corresponding mammalian CCR4 protein (e.g., recombinant proteins). Accordingly, as defined herein, the term includes mature receptor protein, polymorphic or allelic variants, and other isoforms of a mammalian CCR4 (e.g., produced by alternative splicing or other cellular processes), and modified or unmodified forms of the foregoing (e.g., glycosylated, unglycosylated). Mammalian CCR4 proteins can be isolated and/or recombinant proteins (including synthetically produced proteins). Naturally occurring or endogenous mammalian CCR4 proteins include wild type proteins such as mature CCR4, polymorphic or allelic variants and other isoforms which occur naturally in mammals (e.g., humans, non-human primates). Such proteins can be recovered or isolated from a source which naturally produces mammalian CCR4, for example. These proteins and mammalian CCR4 proteins having the same amino acid sequence as a naturally occurring or endogenous corresponding mammalian CCR4, are referred to by the name of the corresponding mammal. For example, where the corresponding mammal is a human, the protein is designated as a human CCR4 protein (e.g., a recombinant human CCR4 produced in a suitable host cell).

"Functional variants" of mammalian CCR4 proteins include functional fragments, functional mutant proteins, and/or functional fusion proteins (e.g., produced via mutagenesis and/or recombinant techniques). Generally, fragments or portions of mammalian CCR4 proteins include those having a deletion (i.e., one or more deletions) of an amino acid (i.e., one or more amino acids) relative to the mature mammalian CCR4 protein (such as N-terminal, C-terminal or internal deletions). Fragments or portions in which only contiguous amino acids have been deleted or in which non-contiguous amino acids have been deleted relative to mature mammalian CCR4 protein are also envisioned.

Generally, mutants of mammalian CCR4 proteins include natural or artificial variants of a mammalian CCR4 protein differing by the addition, deletion and/or substitution of one or more contiguous or non-contiguous amino acid residues (e.g., receptor chimeras). Such mutations can be in a conserved region or nonconserved region (compared to other CXC ($\alpha$) and/or CC ($\beta$) chemokine receptors), extracellular, cytoplasmic, or transmembrane region, for example.

Generally, fusion proteins encompass polypeptides comprising a mammalian CCR4 (e.g., human CCR4) or a variant thereof as a first moiety, linked via a peptide bond to a second moiety not occurring in the mammalian CCR4 as found in nature. Thus, the second moiety can be an amino acid, oligopeptide or polypeptide. The first moiety can be in an N-terminal location, C-terminal location or internal to the fusion protein. In one embodiment, the fusion protein comprises an affinity ligand (e.g., an enzyme, an antigen, epitope tag) as the first moiety, and a second moiety comprising a linker sequence and human CCR4 or a portion thereof.

A "functional fragment or portion", "functional mutant" and/or "functional fusion protein" of a mammalian CCR4 protein refers to an isolated and/or recombinant protein or polypeptide which has at least one function characteristic of a mammalian CCR4 protein as described herein, such as a binding activity, a signaling activity and/or ability to stimulate a cellular response. Preferred functional variants can bind a ligand (i.e., one or more ligands such as TARC, MDC, MCP-1, MIP-1$\alpha$, and/or RANTES), and are referred to herein as "ligand binding variants".

In one embodiment, a functional variant of mammalian CCR4 shares at least about 85% sequence identity with said mammalian CCR4, preferably at least about 90% sequence identity, and more preferably at least about 95% sequence identity with said mammalian CCR4. In another embodiment, a functional fusion protein comprises a first moiety which shares at least about 85% sequence identity with a mammalian CCR4, preferably at least about 90% sequence identity, and more preferably at least about 95% sequence identity with a mammalian CCR4. Sequence identity can be determined using a suitable program, such as the Blastx program (Version 1.4), using appropriate parameters, such as default parameters. In one embodiment, parameters for Blastx search are scoring matrix BLOSUM62, W=3. In another embodiment, a functional variant comprises a nucleic acid sequence which is different from the naturally-occurring nucleic acid molecule but which, due to the degeneracy of the genetic code, encodes mammalian CCR4 or a portion thereof.

A composition comprising an isolated and/or recombinant mammalian CCR4 or functional variant thereof can be maintained under conditions suitable for binding, the mammalian CCR4 or variant is contacted with an antibody or fragment to be tested, and binding is detected or measured directly or indirectly. In one embodiment, cells which naturally express CCR4 or cells comprising a recombinant nucleic acid sequence which encodes a mammalian CCR4 or variant thereof are used. The cells are maintained under conditions appropriate for expression of receptor. The cells are contacted with an antibody or fragment under conditions suitable for binding (e.g., in a suitable binding buffer), and binding is detected by standard techniques. To determine binding, the extent of binding can be determined relative to a suitable control (e.g., compared with background determined in the absence of antibody, compared with binding of a second antibody (i.e., a standard), compared with binding of antibody to untransfected cells). A cellular fraction, such as a membrane fraction, containing receptor or liposomes comprising receptor can be used in lieu of whole cells.

In one embodiment, the antibody is labeled with a suitable label (e.g., fluorescent label, isotope label, antigen or epitope label, enzyme label), and binding is determined by detection of the label. In another embodiment, bound antibody can be detected by labeled second antibody. Specificity of binding can be assessed by competition or displacement, for example, using unlabeled antibody or a ligand as competitor.

Binding inhibition assays can also be used to identify antibodies or fragments thereof which bind CCR4 and inhibit binding of another compound such as a ligand (e.g., TARC, MDC, MCP-1, MIP-1α and/or RANTES) to CCR4 or a functional variant. For example, a binding assay can be conducted in which a reduction in the binding of a ligand of CCR4 (in the presence of an antibody), as compared to binding of the ligand in the absence of the antibody, is detected or measured. A composition comprising an isolated and/or recombinant mammalian CCR4 or functional variant thereof can be contacted with the ligand and antibody simultaneously, or one after the other, in either order. A reduction in the extent of binding of the ligand in the presence of the antibody, is indicative of inhibition of binding by the antibody. For example, binding of the ligand could be decreased or abolished.

In one embodiment, direct inhibition of the binding of a ligand (e.g., a chemokine such as TARC or MDC) to a mammalian CCR4 or variant thereof by an antibody or fragment is monitored. For example, the ability of an antibody to inhibit the binding of $^{125}$I-labeled TARC, $^{125}$I-labeled MDC, $^{125}$I-labeled MCP-1, $^{125}$I-labeled MIP-1α or $^{125}$I-labeled RANTES to mammalian CCR4 can be monitored. Such an assay can be conducted using suitable cells bearing CCR4 or a functional variant thereof, such as isolated blood cells (e.g., T cells) or a suitable cell line naturally expressing CCR4, or a cell line containing nucleic acid encoding a mammalian CCR4, or a membrane fraction from said cells, for instance.

Other methods of identifying the presence of an antibody which binds CCR4 are available, such as other suitable binding assays, or methods which monitor events which are triggered by receptor binding, including signaling function and/or stimulation of a cellular response (e.g., leukocyte trafficking).

It will be understood that the inhibitory effect of antibodies of the present invention can be assessed in a binding inhibition assay. Competition between antibodies for receptor binding can also be assessed in the method. Antibodies which are identified in this manner can be further assessed to determine whether, subsequent to binding, they act to inhibit other functions of CCR4 and/or to assess their therapeutic utility.

Signaling Assays

The binding of a ligand or promoter, such as an agonist, to CCR4 can result in signaling by this G protein-coupled receptor, and the activity of G proteins as well as other intracellular signaling molecules is stimulated. The induction of signaling function by a compound (e.g., an antibody or fragment thereof) can be monitored using any suitable method. Such an assay can be used to identify antibody agonists of CCR4. The inhibitory activity of an antibody or functional fragment thereof can be determined using a ligand or promoter in the assay, and assessing the ability of the antibody to inhibit the activity induced by ligand or promoter.

G protein activity, such as hydrolysis of GTP to GDP, or later signaling events triggered by receptor binding, such as induction of rapid and transient increase in the concentration of intracellular (cytosolic) free calcium $[Ca^{2+}]_i$, can be assayed by methods known in the art or other suitable methods (see e.g., Neote, K. et al., *Cell,* 72: 415–425 1993); Van Riper et al., *J. Exp. Med.,* 177: 851–856 (1993); Dahinden, C. A. et al., *J. Exp. Med.,* 179: 751–756 (1994)).

For example, the functional assay of Sledziewski et al. using hybrid G protein coupled receptors can be used to monitor the ability a ligand or promoter to bind receptor and activate a G protein (Sledziewski et al., U.S. Pat. No. 5,284,746, the teachings of which are incorporated herein by reference).

Such assays can be performed in the presence of the antibody or fragment thereof to be assessed, and the ability of the antibody or fragment to inhibit the activity induced by the ligand or promoter is determined using known methods and/or methods described herein.

Chemotaxis and Assays of Cellular Stimulation

Chemotaxis assays can also be used to assess the ability of an antibody or functional fragment thereof to block binding of a ligand to mammalian CCR4 or functional variant thereof and/or inhibit function associated with binding of the ligand to the receptor. These assays are based on the functional migration of cells in vitro or in vivo induced by a compound. Chemotaxis can be assessed as described in the Examples, e.g., in an assay utilizing a 96-well chemotaxis plate, or using other art-recognized methods for assessing chemotaxis. For example, the use of an in vitro transendothelial chemotaxis assay is described by Springer et al. (Springer et al., WO 94/20142, published Sep. 15, 1994, the teachings of which are incorporated herein by reference; see also Berman et al., *Immunol. Invest.* 17: 625–677 (1988)). Migration across endothelium into collagen gels has also been described (Kavanaugh et al., *J. Immunol.,* 146: 4149–4156 (1991)). Stable transfectants of mouse L1.2 pre-B cells or of other suitable host cells capable of chemotaxis can be used in chemotaxis assays, for example.

Generally, chemotaxis assays monitor the directional movement or migration of a suitable cell (such as a leukocyte (e.g., lymphocyte, eosinophil, basophil)) into or through a barrier (e.g., endothelium, a filter), toward increased levels of a compound, from a first surface of the barrier toward an opposite second surface. Membranes or filters provide convenient barriers, such that the directional movement or migration of a suitable cell into or through a filter, toward increased levels of a compound, from a first surface of the filter toward an opposite second surface of the filter, is monitored. In some assays, the membrane is coated with a substance to facilitate adhesion, such as ICAM-1, fibronectin or collagen. Such assays provide an in vitro approximation of leukocyte "homing".

For example, one can detect or measure inhibition of the migration of cells in a suitable container (a containing means), from a first chamber into or through a microporous membrane into a second chamber which contains an antibody to be tested, and which is divided from the first chamber by the membrane. A suitable membrane, having a suitable pore size for monitoring specific migration in response to compound, including, for example, nitrocellulose, polycarbonate, is selected. For example, pore sizes of about 3–8 microns, and preferably about 5–8 microns can be used. Pore size can be uniform on a filter or within a range of suitable pore sizes.

To assess migration and inhibition of migration, the distance of migration into the filter, the number of cells crossing the filter that remain adherent to the second surface of the filter, and/or the number of cells that accumulate in the second chamber can be determined using standard techniques (e.g., microscopy). In one embodiment, the cells are labeled with a detectable label (e.g., radioisotope, fluorescent label, antigen or epitope label), and migration can be assessed in the presence and absence of the antibody or fragment by determining the presence of the label adherent to the membrane and/or present in the second chamber using an appropriate method (e.g., by detecting radioactivity, fluorescence, immunoassay). The extent of migration induced by an antibody agonist can be determined relative to a suitable control (e.g., compared to background migration determined in the absence of the antibody, compared to the extent of migration induced by a second compound (i.e., a standard), compared with migration of untransfected cells induced by the antibody).

In one embodiment, particularly for T cells, monocytes or cells expressing a mammalian CCR4, transendothelial migration can be monitored. In this embodiment, transmigration through an endothelial cell layer is assessed. To prepare the cell layer, endothelial cells can be cultured on a microporous filter or membrane, optionally coated with a substance such as collagen, fibronectin, or other extracellular matrix proteins, to facilitate the attachment of endothelial cells. Preferably, endothelial cells are cultured until a confluent monolayer is formed. A variety of mammalian endothelial cells can are available for monolayer formation, including for example, vein, artery or microvascular endothelium, such as human umbilical vein endothelial cells (Clonetics Corp, San Diego, Calif.). To assay chemotaxis in response to a particular mammalian receptor, endothelial cells of the same mammal are preferred; however endothelial cells from a heterologous mammalian species or genus can also be used.

Generally, the assay is performed by detecting the directional migration of cells into or through a membrane or filter, in a direction toward increased levels of a compound, from a first surface of the filter toward an opposite second surface of the filter, wherein the filter contains an endothelial cell layer on a first surface. Directional migration occurs from the area adjacent to the first surface, into or through the membrane, towards a compound situated on the opposite side of the filter. The concentration of compound present in the area adjacent to the second surface, is greater than that in the area adjacent to the first surface.

In one embodiment used to test for an antibody inhibitor, a composition comprising cells capable of migration and expressing a mammalian CCR4 receptor can be placed in the first chamber. A composition comprising one or more ligands or promoters capable of inducing chemotaxis of the cells in the first chamber (having chemoattractant function) is placed in the second chamber. Preferably shortly before the cells are placed in the first chamber, or simultaneously with the cells, a composition comprising the antibody to be tested is placed, preferably, in the first chamber. Antibodies or functional fragments thereof which can bind receptor and inhibit the induction of chemotaxis, by a ligand or promoter, of the cells expressing a mammalian CCR4 in this assay are inhibitors of receptor function (e.g., inhibitors of stimulatory function). A reduction in the extent of migration induced by the ligand or promoter in the presence of the antibody or fragment is indicative of inhibitory activity. Separate binding studies (see above) could be performed to determine whether inhibition is a result of binding of the antibody to receptor or occurs via a different mechanism.

In vivo assays which monitor leukocyte infiltration of a tissue, in response to injection of a compound (e.g., chemokine or antibody) in the tissue, are described below (see Models of Inflammation). These models of in vivo homing measure the ability of cells to respond to a ligand or promoter by emigration and chemotaxis to a site of inflammation and to assess the ability of an antibody or fragment thereof to block this emigration.

In addition to the methods described, the effects of an antibody or fragment on the stimulatory function of CCR4 can be assessed by monitoring cellular responses induced by active receptor, using suitable host cells containing receptor.

Identification of Additional Ligands, Inhibitors and/or Promoters of Mammalian CCR4 Function The assays described above, which can be used to assess binding and function of the antibodies and fragments of the present invention, can be adapted to identify additional ligands or other substances which bind a mammalian CCR4 or functional variant thereof, as well as inhibitors and/or promoters of mammalian CCR4 function. For example, agents having the same or a similar binding specificity as that of an antibody of the present invention or functional portion thereof can be identified by a competition assay with said antibody or portion thereof. Thus, the present invention also encompasses methods of identifying ligands of the receptor or other substances which bind a mammalian CCR4 protein, as well as inhibitors (e.g., antagonists) or promoters (e.g., agonists) of receptor function. In one embodiment, cells bearing a mammalian CCR4 protein or functional variant thereof (e.g., leukocytes, cell lines or suitable host cells which have been engineered to express a mammalian CCR4 protein or functional variant encoded by a nucleic acid introduced into said cells) are used in an assay to identify and assess the efficacy of ligands or other substances which bind receptor, including inhibitors or promoters of receptor function. Such cells are also useful in assessing the function of the expressed receptor protein or polypeptide.

According to the present invention, ligands and other substances which bind receptor, inhibitors and promoters of receptor function can be identified in a suitable assay, and further assessed for therapeutic effect. Inhibitors of receptor function can be used to inhibit (reduce or prevent) receptor activity, and ligands and/or promoters can be used to induce (trigger or enhance) normal receptor function where indicated. Thus, the present invention provides a method of treating inflammatory diseases, including autoimmune disease and graft rejection, comprising administering an inhibitor of receptor function to an individual (e.g., a mammal). The present invention further provides a method of stimulating receptor function by administering a novel ligand or promoter of receptor function to an individual, providing a new approach to selective stimulation of leukocyte function, which is useful, for example, in the treatment of infectious diseases and cancer.

As used herein, a "ligand" of a mammalian CCR4 protein refers to a particular class of substances which bind to a mammalian CCR4 protein, including natural ligands and synthetic and/or recombinant forms of natural ligands. Infectious agents having a tropism for mammalian CCR4-positive cells (e.g., viruses such as HIV) can also bind to a mammalian CCR4 protein. A natural ligand of a selected mammalian receptor is of a mammalian origin which is the same as that of the mammalian CCR4 protein (e.g., a chemokine such as TARC, MDC, MCP-1, MIP-1α and/or RANTES). In a preferred embodiment, ligand binding of a mammalian CCR4 protein occurs with high affinity.

As used herein, an "inhibitor" is a substance which inhibits (decreases or prevents) at least one function characteristic of a mammalian CCR4 protein (e.g., a human CCR4), such as a binding activity (e.g., ligand binding, promoter binding, antibody binding), a signaling activity (e.g., activation of a mammalian G protein, induction of rapid and transient increase in the concentration of cytosolic free calcium $[Ca^{2+}]_i$), and/or cellular response function (e.g., stimulation of chemotaxis, exocytosis or inflammatory mediator release by leukocytes). An inhibitor is also a substance which inhibits HIV entry into a cell. The term inhibitor refers to substances including antagonists which bind receptor (e.g., an antibody, a mutant of a natural ligand, small molecular weight organic molecules, other competitive inhibitors of ligand binding), and substances which inhibit receptor function without binding thereto (e.g., an anti-idiotypic antibody).

As used herein, a "promoter" is a substance which promotes (induces, causes, enhances or increases) at least one function characteristic of a mammalian CCR4 protein (e.g., a human CCR4), such as a binding activity (e.g., ligand, inhibitor and/or promoter binding), a signaling activity (e.g., activation of a mammalian G protein, induction of rapid and transient increase in the concentration of cytosolic free calcium $[Ca^{2+}]_i$), and/or a cellular response function (e.g., stimulation of chemotaxis, exocytosis or inflammatory mediator release by leukocytes). The term promoter refers to substances including agonists which bind receptor (e.g., an antibody, a homolog of a natural ligand from another species), and substances which promote receptor function without binding thereto (e.g., by activating an associated protein). In a preferred embodiment, the agonist is other than a homolog of a natural ligand.

Thus, the invention also relates to a method of detecting or identifying an agent which binds a mammalian CC-chemokine receptor 4 or ligand binding variant thereof, including ligands, inhibitors, promoters, and other substances which bind a mammalian CCR4 receptor or functional variant. According to the method, an agent to be tested, an antibody or antigen-binding fragment of the present invention (e.g., 1G1, 2B10, an antibody having an epitopic specificity which is the same as or similar to that of 1G1 or 2B10, and antigen-binding fragments thereof) and a composition comprising a mammalian CC-chemokine receptor 4 or a ligand binding variant thereof can be combined. The foregoing components are combined under conditions suitable for binding of the antibody or antigen-binding fragment to mammalian CC-chemokine receptor 4 or a ligand binding variant thereof, and binding of the antibody or fragment to the mammalian CC-chemokine receptor 4 or ligand binding variant is detected or measured, either directly or indirectly, according to methods described herein or other suitable methods. A decrease in the amount of complex formed relative to a suitable control (e.g., in the absence of the agent to be tested) is indicative that the agent binds said receptor or variant. The composition comprising a mammalian CC-chemokine receptor 4 or a ligand binding variant thereof can be a membrane fraction of a cell bearing recombinant chemokine receptor 4 protein or ligand binding variant thereof. The antibody or fragment thereof can be labeled with a label such as a radioisotope, spin label, antigen or epitope label, enzyme label, fluorescent group and chemiluminescent group.

In one embodiment, the invention relates to a method of detecting or identifying an agent which binds a mammalian CC-chemokine receptor 4 or a ligand binding variant thereof, comprising combining an agent to be tested, an antibody or antigen-binding fragment of the present invention (e.g., 1G1, 2B10, an antibody having an epitopic specificity which is the same as or similar to that of 1G1 or 2B10, or antigen-binding fragments thereof) and a cell bearing a mammalian CC-chemokine receptor 4 or a ligand binding variant thereof. The foregoing components are combined under conditions suitable for binding of the antibody or antigen-binding fragment to the CCR4 protein or ligand binding variant thereof, and binding of the antibody or fragment to the mammalian CC-chemokine receptor 4 or variant is detected or measured, either directly or indirectly, by methods described herein and or other suitable methods. A decrease in the amount of complex formed relative to a suitable control is indicative that the agent binds the receptor or variant. The antibody or fragment thereof can be labeled with a label selected from the group consisting of a radioisotope, spin label, antigen or epitope label, enzyme label, fluorescent group and chemiluminescent group. These and similar assays can be used to detect agents, including ligands (e.g., chemokines or strains of HIV which interact with CCR4) or other substances, including inhibitors or promoters of receptor function, which can bind CCR4 and compete with the antibodies described herein for binding to the receptor.

The assays described above can be used, alone or in combination with each other or other suitable methods, to identify ligands or other substances which bind a mammalian CCR4 protein, and inhibitors or promoters of a mammalian CCR4 protein or variant. The in vitro methods of the present invention can be adapted for high-throughput screening in which large numbers of samples are processed (e.g., a 96-well format). Cells expressing mammalian CCR4 (e.g., human CCR4) at levels suitable for high-throughput screening can be used, and thus, are particularly valuable in the identification and/or isolation of ligands or other substances which bind receptor, and inhibitors or promoters of mammalian CCR4 proteins. Expression of receptor can be monitored in a variety of ways. For instance, expression can be monitored using antibodies of the present invention which bind receptor or a portion thereof. Also, commercially available antibodies can be used to detect expression of an antigen- or epitope-tagged fusion protein comprising a receptor protein or polypeptide (e.g., FLAG tagged receptors), and cells expressing the desired level can be selected.

Nucleic acid encoding a mammalian CCR4 protein or functional variant thereof can be incorporated into an expression system to produce a receptor protein or polypeptide. An isolated and/or recombinant mammalian CCR4 protein or variant, such as a receptor expressed in cells stably or transiently transfected with a construct comprising a recombinant nucleic acid encoding a mammalian CCR4 protein or variant, or in a cell fraction containing receptor (e.g., a membrane fraction from transfected cells, liposomes incorporating receptor), can be used in tests for receptor function. The receptor can be further purified if desired. Testing of receptor function can be carried out in vitro or in vivo.

An isolated and/or recombinant mammalian CCR4 protein or functional variant thereof, such as a human CCR4, can be used in the present method, in which the effect of a compound is assessed by monitoring receptor function as described herein or using other suitable techniques. For example, stable or transient transfectants (e.g., baculovirus infected Sf9 cells, stable tranfectants of mouse L1.2 pre-B cells), can be used in binding assays. Stable transfectants of Jurkat cells or of other suitable cells capable of chemotaxis can be used (e.g., mouse L1.2 pre-B cells) in chemotaxis assays, for example.

According to the method of the present invention, compounds can be individually screened or one or more compounds can be tested simultaneously according to the methods herein. Where a mixture of compounds is tested, the compounds selected by the processes described can be separated (as appropriate) and identified by suitable methods (e.g., PCR, sequencing, chromatography, mass spectroscopy). The presence of one or more compounds (e.g., a ligand, inhibitor, promoter) in a test sample can also be determined according to these methods.

Large combinatorial libraries of compounds (e.g., organic compounds, recombinant or synthetic peptides, "peptoids", nucleic acids) produced by combinatorial chemical synthesis or other methods can be tested (see e.g., Zuckerman, R. N. et al., *J. Med. Chem.*, 37: 2678–2685 (1994) and references cited therein; see also, Ohlmeyer, M. H. J. et al., *Proc. Natl. Acad. Sci. USA* 90:10922–10926 (1993) and DeWitt, S. H. et al., *Proc. Natl. Acad. Sci. USA* 90:6909–6913 (1993), relating to tagged compounds; Rutter, W. J. et al. U.S. Pat. No. 5,010,175; Huebner, V. D. et al., U.S. Pat. No. 5,182,366; and Geysen, H. M., U.S. Pat. No. 4,833,092). Where compounds selected from a combinatorial library by the present method carry unique tags, identification of individual compounds by chromatographic methods is possible.

In one embodiment, phage display methodology is used. For example, a mammalian CCR4 protein or functional variant, an antibody or functional portion thereof of the present invention, and a phage (e.g., a phage or collection of phage such as a library) displaying a polypeptide, can be combined under conditions appropriate for binding of the antibody or portion thereof to the mammalian CCR4 protein or variant (e.g., in a suitable binding buffer). Phage which can compete with the antibody or portion thereof and bind to the mammalian CCR4 protein or variant can be detected or selected using standard techniques or other suitable methods. Bound phage can be separated from receptor using a suitable elution buffer. For example, a change in the ionic strength or pH can lead to a release of phage. Alternatively, the elution buffer can comprise a release component or components designed to disrupt binding of compounds e.g., one or more compounds which can disrupt binding of the displayed peptide to the receptor, such as a ligand, inhibitor, and/or promoter which competitively inhibits binding). Optionally, the selection process can be repeated or another selection step can be used to further enrich for phage which bind receptor. The displayed polypeptide can be characterized (e.g., by sequencing phage DNA). The polypeptides identified can be produced and further tested for binding, and for inhibitor or promoter function. Analogs of such peptides can be produced which will have increased stability or other desirable properties.

In one embodiment, phage expressing and displaying fusion proteins comprising a coat protein with an N-terminal peptide encoded by random sequence nucleic acids can be produced. Suitable host cells expressing a mammalian CCR4 protein or variant and an anti-CCR4 antibody or functional portion thereof, are combined with the phage, bound phage are selected, recovered and characterized. (See e.g., Doorbar and Winter, *J. Mol. Biol.* 244:361 (1994), discussing a phage display procedure used with a G protein-coupled receptor, and WO 97/08320 (Morphosys), published Mar. 6, 1997).

Other sources of potential ligands or other substances which bind to, or inhibitors and/or promoters of, mammalian CCR4 proteins include, but are not limited to, variants of CCR4 ligands, including naturally occurring, synthetic or recombinant variants of TARC, MDC, MCP-1, MIP-1α and/or RANTES, substances such as other chemoattractants or chemokines, variants thereof, low molecular weight organic molecules, other inhibitors and/or promoters (e.g., anti-CCR4 antibodies, antagonists, agonists), other G protein-coupled receptor ligands, inhibitors and/or promoters (e.g., antagonists or agonists), and soluble portions of a mammalian CCR4 receptor, such as a suitable receptor peptide or analog which can inhibit receptor function (see e.g., Murphy, R. B., WO 94/05695).

Models of Inflammation

In vivo models of inflammation are available which can be used to assess the effects of antibodies and fragments of the invention in vivo as therapeutic agents. For example, leukocyte infiltration upon intradermal injection of a chemokine and an antibody or fragment thereof reactive with mammalian CCR4 into a suitable animal, such as rabbit, mouse, rat, guinea pig or rhesus macaque can be monitored (see e.g., Van Damme, J. et al.,*J. Exp. Med.,* 176: 59–65 (1992); Zachariae, C. O. C. et al., *J. Exp. Med.* 171: 2177–2182 (1990); Jose, P. J. et al., *J. Exp. Med.* 179: 881–887 (1994)). In one embodiment, skin biopsies are assessed histologically for infiltration of leukocytes (e.g., eosinophils, granulocytes). In another embodiment, labeled cells (e.g., stably transfected cells expressing a mammalian CCR4, labeled with $^{111}$In for example) capable of chemotaxis and extravasation are administered to the animal. For example, an antibody or fragment to be assessed can be administered, either before, simultaneously with or after ligand or agonist is administered to the test animal. A decrease of the extent of infiltration in the presence of antibody as compared with the extent of infiltration in the absence of inhibitor is indicative of inhibition.

Diagnostic and Therapeutic Applications

The antibodies and fragments of the present invention are useful in a variety of applications, including research, diagnostic and therapeutic applications. In one embodiment, the antibodies are labeled with a suitable label (e.g., fluorescent label, chemiluminescent label, isotope label, antigen or epitope label or enzyme label). For instance, they can be used to isolate and/or purify receptor or portions thereof, and to study receptor structure (e.g., conformation) and function.

In addition, the various antibodies of the present invention can be used to detect CCR4 or to measure the expression of receptor, for example, on T cells (e.g., CD8+ cells, CD45RO+ cells), monocytes and/or on cells transfected with a receptor gene. Thus, they also have utility in applications such as cell sorting (e.g., flow cytometry, fluorescence activated cell sorting), for diagnostic or research purposes.

The anti-CCR4 antibodies of the present invention have value in diagnostic applications. An anti-CCR4 antibody or fragment thereof can be used to monitor expression of this receptor in individuals, similar to the way anti-CD4 has been used as a diagnostic indicator of HIV stage.

Typically, diagnostic assays entail detecting the formation of a complex resulting from the binding of an antibody or fragment thereof to CCR4. For diagnostic purposes, the antibodies or antigen-binding fragments can be labeled or unlabeled. The antibodies or fragments can be directly labeled. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat.

Nos. 3,817,827; 3,850,752; 3,901,654 and 4,098,876). When unlabeled, the antibodies or fragments can be detected using suitable means, as in agglutination assays, for example. Unlabeled antibodies or fragments can also be used in combination with another (i.e., one or more) suitable reagent which can be used to detect antibody, such as a labeled antibody (e.g., a second antibody) reactive with the first antibody (e.g., anti-idiotype antibodies or other antibodies that are specific for the unlabeled immunoglobulin) or other suitable reagent (e.g., labeled protein A).

In one embodiment, the antibodies or fragments of the present invention can be utilized in enzyme immunoassays, wherein the subject antibody or fragment, or second antibodies, are conjugated to an enzyme. When a biological sample comprising a mammalian CCR4 protein is combined with the subject antibodies, binding occurs between the antibodies and CCR4 protein. In one embodiment, a sample containing cells expressing a mammalian CCR4 protein, such as human blood, is combined with the subject antibodies, and binding occurs between the antibodies and cells bearing a human CCR4 protein comprising an epitope recognized by the antibody. These bound cells can be separated from unbound reagents and the presence of the antibody-enzyme conjugate specifically bound to the cells can be determined, for example, by contacting the sample with a substrate of the enzyme which produces a color or other detectable change when acted on by the enzyme. In another embodiment, the subject antibodies can be unlabeled, and a second, labeled antibody can be added which recognizes the subject antibody.

Kits for use in detecting the presence of a mammalian CCR4 protein in a biological sample can also be prepared. Such kits will include an antibody or functional fragment thereof which binds to a mammalian CC-chemokine receptor 4 or portion of said receptor, as well as one or more ancillary reagents suitable for detecting the presence of a complex between the antibody or fragment and CCR4 or portion thereof. The antibody compositions of the present invention can be provided in lyophilized form, either alone or in combination with additional antibodies specific for other epitopes. The antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the antibodies can be provided as a lyophilized mixture with the adjunct ingredients, or the adjunct ingredients can be separately provided for combination by the user. Generally these adjunct materials will be present in less than about 5% weight based on the amount of active antibody, and usually will be present in a total amount of at least about 0.001% weight based on antibody concentration. Where a second antibody capable of binding to the monoclonal antibody is employed, such antibody can be provided in the kit, for instance in a separate vial or container. The second antibody, if present, is typically labeled, and can be formulated in an analogous manner with the antibody formulations described above.

Similarly, the present invention also relates to a method of detecting and/or quantitating expression of a mammalian CCR4 or a portion of the receptor by a cell, in which a composition comprising a cell or fraction thereof (e.g., membrane fraction) is contacted with an antibody or functional fragment thereof (e.g., 1G1 and/or 2B10) which binds to a mammalian CCR4 or portion of the receptor under conditions appropriate for binding of the antibody or fragment thereto, and binding is monitored. Detection of the antibody, indicative of the formation of a complex between antibody and CCR4 or a portion thereof, indicates the presence of the receptor. Binding of antibody to the cell can be determined as described above under the heading "Binding Assays", for example. The method can be used to detect expression of CCR4 on cells from an individual (e.g., in a sample, such as a body fluid, such as blood, saliva or other suitable sample). The level of expression of CCR4 on the surface of T cells or monocytes can also be determined, for instance, by flow cytometry, and the level of expression (e.g., staining intensity) can be correlated with disease susceptibility, progression or risk.

Chemokine receptors function in the migration of leukocytes throughout the body, particularly to inflammatory sites. Inflammatory cell emigration from the vasculature is regulated by a three-step process involving interactions of leukocyte and endothelial cell adhesion proteins and cell specific chemoattractants and activating factors (Springer, T. A., *Cell,* 76:301–314 (1994); Butcher, E. C., *Cell,* 67:1033–1036 (1991); Butcher, E. C. and Picker, L. J., *Science* (*Wash. D.C.*), 272:60–66 (1996)). These are: (a) a low affinity interaction between leukocyte selectins and endothelial cell carbohydrates; (b) a high-affinity interaction between leukocyte chemoattractant receptors and chemoattractant/activating factors; and (c) a tight-binding between leukocyte integrins and endothelial cell adhesion proteins of the immunoglobulin superfamily. Different leukocyte subsets express different repertoires of selectins, chemoattractant receptors and integrins. Additionally, inflammation alters the expression of endothelial adhesion proteins and the expression of chemoattractant and leukocyte activating factors. As a consequence, there is a great deal of diversity for regulating the selectivity of leukocyte recruitment to extravascular sites. The second step is crucial in that the activation of the leukocyte chemoattractant receptors is thought to cause the transition from the selectin-mediated cell rolling to the integrin-mediated tight binding. This results in the leukocyte being ready to transmigrate to perivascular sites. The chemoattractant/chemoattractant receptor interaction is also crucial for transendothelial migration and localization within a tissue (Campbell, J. J., et al., *J. Cell Biol.,* 134:255–266 (1996); Carr, M. W., et al., *Immunity,* 4:179–187 (1996)). This migration is directed by a concentration gradient of chemoattractant leading towards the inflammatory focus.

CCR4 has an important role in leukocyte trafficking. It is likely that CCR4 is a key chemokine receptor for T cell or T cell subset or monocyte migration to certain inflammatory sites, and so anti-CCR4 mAbs can be used to inhibit (reduce or prevent) T cell or monocyte migration, particularly that associated with T cell dysfunction, such as autoimmune disease or allergic reactions, or with monocyte-mediated disorders such as atherosclerosis. Accordingly, the antibodies and fragments thereof of the present invention can also be used to modulate receptor function in research and therapeutic applications. For instance, the antibodies and functional fragments described herein can act as inhibitors to inhibit (reduce or prevent) (a) binding (e.g., of a ligand, an inhibitor or a promoter) to the receptor, (b) a receptor signaling function, and/or (c) a stimulatory function. Antibodies which act as inhibitors of receptor function can block ligand or promoter binding directly or indirectly (e.g., by causing a conformational change). For example, antibodies can inhibit receptor function by inhibiting binding of a ligand, or by desensitization (with or without inhibition of binding of a ligand). Antibodies which bind receptor can also act as agonists of receptor function, triggering or stimulating a receptor function, such as a signaling and/or a stimulatory function of a receptor (e.g., leukocyte trafficking) upon binding to receptor.

Thus, the present invention provides a method of inhibiting leukocyte trafficking in a mammal (e.g., a human patient), comprising administering to the mammal an effective amount of an antibody or functional fragment of the present invention. Administration of an antibody or fragment of the present invention can result in amelioration or elimination of the disease state.

The antibody of the present invention, or a functional fragment thereof, can also be used to treat disorders in which activation of the CCR4 receptor by binding of chemokines is implicated. For example, the antibodies or functional fragments thereof (e.g., 1G1 and/or 2B10 or functional fragments thereof) can be used to treat allergy, atherogenesis, anaphylaxis, malignancy, chronic and acute inflammation, histamine and IgE-mediated allergic reactions, shock, and rheumatoid arthritis, atherosclerosis, multiple sclerosis, allograft rejection, fibrotic disease, asthma, and inflammatory glomerulopathies.

Diseases or conditions of humans or other species which can be treated with inhibitors of CCR4 receptor function (including antibodies or suitable fragments thereof), include, but are not limited to:

inflammatory or allergic diseases and conditions, including respiratory allergic diseases such as asthma, allergic rhinitis, hypersensitivity lung diseases, hypersensitivity pneumonitis, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); anaphylaxis or hypersensitivity responses, drug allergies (e.g., to penicillin, cephalosporins), insect sting allergies; inflammatory bowel diseases, such as Crohn's disease and ulcerative colitis; spondyloarthropathies; scleroderma; psoriasis and inflammatory dermatoses such as dermatitis, eczema, atopic dermatitis, allergic contact dermatitis, urticaria; vasculitis (e.g., necrotizing, cutaneous, and hypersensitivity vasculitis);

autoimmune diseases, such as arthritis (e.g., rheumatoid arthritis, psoriatic arthritis), multiple sclerosis, systemic lupus erythematosus, myasthenia gravis, juvenile onset diabetes, nephritides such as glomerulonephritis, autoimmune thyroiditis, Behcet's disease;

graft rejection (e.g., in transplantation), including allograft rejection or graft-versus-host disease;

atherosclerosis;

cancers with leukocyte infiltration of the skin or organs;

other diseases or conditions (including CCR4-mediated diseases or conditions), in which undesirable inflammatory responses are to be inhibited can be treated, including, but not limited to, reperfusion injury, certain hematologic malignancies, cytokine-induced toxicity (e.g., septic shock, endotoxic shock), polymyositis, dermatomyositis, and granulomatous diseases including sarcoidosis.

Diseases or conditions of humans or other species which can be treated with promoters of CCR4 receptor function (including antibodies or fragments thereof), include, but are not limited to:

immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; and immunosuppression due congenital deficiency in receptor function or other causes.

Anti-CCR4 antibodies of the present invention can block the binding of one or more chemokines, thereby blocking the downstream cascade of one or more events leading to the above disorders.

Modes of Administration

One or more antibodies or fragments of the present invention can be administered to an individual by an appropriate route, either alone or in combination with (before, simultaneous with, or after) another drug or agent. For example, the antibodies of the present invention can also be used in combination with other monoclonal or polyclonal antibodies (e.g., in combination with antibodies which bind other chemokine receptors, including, but not limited to, CCR3 and CCR5) or with existing blood plasma products, such as commercially available gamma globulin and immune globulin products used in prophylactic or therapeutic treatments. The antibodies or fragments of the present invention can be used as separately administered compositions given in conjunction with antibiotics and/or antimicrobial agents.

An effective amount of an antibody or fragment (i.e., one or more antibodies or fragments) is administered. An effective amount is an amount sufficient to achieve the desired therapeutic (including prophylactic) effect, under the conditions of administration, such as an amount sufficient for inhibition of a CCR4 function, and thereby, inhibition of an inflammatory response or HIV infection, or an amount sufficient for promotion of a CCR4 function, as indicated.

A variety of routes of administration are possible including, but not necessarily limited to, oral, dietary, topical, parenteral (e.g., intravenous, intraarterial, intramuscular, subcutaneous injection), inhalation (e.g., intrabronchial, intraocular, intranasal or oral inhalation, intranasal drops), depending on the disease or condition to be treated. Other suitable methods of administration can also include rechargeable or biodegradable devices and slow release polymeric devices. The pharmaceutical compositions of this invention can also be administered as part of a combinatorial therapy with other agents.

Formulation of an antibody or fragment to be administered will vary according to the route of administration and formulation (e.g., solution, emulsion, capsule) selected. An appropriate pharmaceutical composition comprising an antibody or functional fragment thereof to be administered can be prepared in a physiologically acceptable vehicle or carrier. A mixture of antibodies and/or fragments can also be used. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. A variety of appropriate aqueous carriers are known to the skilled artisan, including water, buffered water, buffered saline, polyols (e.g., glycerol, propylene glycol, liquid polyethylene glycol), dextrose solution and glycine. Intravenous vehicles can include various additives, preservatives, or fluid, nutrient or electrolyte replenishers (See, generally, *Remington's Pharmaceutical Science,* 16th Edition, Mack, Ed. 1980). The compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate. The antibodies and fragments of this invention can be lyophilized for storage and reconstituted in a suitable carrier prior to use according to art-known lyophilization and reconstitution techniques. The optimum concentration of the active ingredient(s) in the chosen medium can be determined empirically, according to procedures well known to the skilled artisan, and will depend on the ultimate pharmaceutical formulation desired. For inhalation, the antibody or fragment can be solubilized and loaded into a suitable dispenser for administration (e.g., an atomizer, nebulizer or pressurized aerosol dispenser).

The invention will now be further illustrated by the following examples, which are not intended to limit the scope of the invention. The teachings of all references cited herein are incorporated herein in their entirety.

EXAMPLES

Materials and Methods

Construction of CCR4 Stable Transfectants

CCR4 cDNA was obtained by PCR using a 5'-oligonucleotide primer (5'-CCAACCAAGCTTATGAACCCCACGGATATAGCAG-3'; SEQ ID NO: 1) and 3'-oligonucleotide primer (5'-CCAACCTCTAGATTAGAGCATCATGGAGATCATG ATCC-3'; SEQ ID NO: 2) which contained flanking HindIII and XbaI sites, respectively. The PCR fragment was subcloned into the HindIII and XbaI sites of pMRB101, in which the inserted gene was driven by a CMV promoter. The DNA was stably transfected into a murine pre-B lymphoma cell line (L1.2 or L1/2) as described (Ponath et al., *J. Exp. Med.* 183:2437 (1996); Wu et al., *J. Biol. Chem.* 271:31202 (1996); Wu et al., *Nature* 384:179 (1996)). The cells that expressed high levels of CCR4 were selected by serial dilution/subcloning for their ability to chemotax to TARC and MDC. For monoclonal antibody production, the cells were treated with 5 mM butyric acid for 16–18 hours and used for immunizing mice.

Cells and Cell Lines

Venous blood was collected from volunteer donors and PBMC were isolated by ficoll-hypaque density gradient centrifugation as described (Ponath et al., *J. Exp. Med.* 183:2437 (1996)). Other cell lines used included transfectants of the L1.2 murine pre-B lymphoma cells expressing various chemokine receptors or orphan G-protein-coupled receptors.

Human peripheral blood was collected in 10% (v/v) 0.1M EDTA, layered onto 1-Step Polymorphs gradient (Accurate Chemical Co., NY) and centrifuged at 400×g for 30 minutes at room temperature. Neutrophil and mononuclear cell layers were collected, re-suspended in DPBS without calcium and magnesium (Life Technologies, Grand Island, N.Y.) and centrifuged for 15 minutes at −750×g. Red blood cells were lysed in the neutrophil fraction by re-suspending the pellet in E-Lyse (Cardinal Associates, Santa Fe, N.Mex.) for 5 minutes on ice. Both cell fractions were washed 2 times with ice cold DPBS. CD14 positive monocytes were removed from the peripheral mononuclear cells by incubation for 30 minutes at 4° C. of $10^7$ mononuclear cells in PBS 1% BSA 5 mM EDTA at $5×10^7$ cells/ml with CD14 Miltenyi beads (Miltenyi Biotech Auburn, Calif.) where 20 μl of beads were used per mononuclear cells. They were then spun down, re-suspended in PBS, 1% BSA, 5 mM EDTA at $5×10^7$ cells/ml and passed over a VS column (Miltenyi Biotech Auburn, Calif.) in a magnetic field to remove non-tagged cells. Cells were removed by forcing 5 ml of PBS, 1% BSA, 5 MM EDTA over the VS column, outside the magnetic field. The procedure was repeated using CD4 Miltenyi beads to isolate CD4 lymphocytes which were incubated overnight in DMEM, 2 nM glutamine, penicillin 50 U/ml, streptomycin 50 μg/ml, MEM sodium pyruvate 1 nM, Hepes 10 nM (all from Gibco BRL, Grand Island, N.Y. 14072) with 10% FCS (Hyclone, Utah 84321) before use in chemotaxis assays.

Preparation of Chronically Activated TH1 and TH2 Lymphocytes

Six-well tissue culture plates (Falcon 3046, Beckton Dickinson Labware, Franklin Lakes, N.J.) were coated overnight with 10 μg/ml anti-CD28 (Beckton Dickinson) and 2 μg/ml OKT3 (American Type Culture Collection, Manassas, Va.) and then washed twice with PBS. Umbilical cord blood CD4 lymphocytes (Poietic Systems, German Town, Md.) were cultured at $10^5$–$10^6$ cells/ml in DMEM, 2 nM glutamine, penicilin 50 U/ml, streptomycin 50 ug/ml, MEM sodium pyruvate 1 nM, Hepes 10 nM (all from Gibco BRL, Grand Island N.Y.) with 10% FCS (Hyclone, Utah) and IL-2 (4 ng/ml). IL-12 (5 ng/ml) and anti-IL4 (1 mg/ml) were used to direct to TH1, while IL-4 (5 ng/ml) and anti-IFN gamma (1 ug/ml) were used to direct to TH2. After 4–5 days, the activated TH1 and TH2 lymphocytes were washed once in DMEM and cultured for 4–7 days in DMEM with 10% FBS and IL-2 (1 ng/ml). Following this, the activated TH1 and TH2 lymphocytes were re-stimulated for 5 days with anti-CD28/OKT3 and cytokines as described above, but with the addition of anti-CD95L (1 mg/ml) to prevent apoptosis. After 4–5 days, the TH1 and TH2 lymphocytes were washed and then cultured again with IL-2 for 4 days. Activated TH1 and TH2 lymphocytes were maintained in this way for a maximum of three cycles. All cytokines were obtained from R and D Systems (Minneapolis, Minn.), while anti-IL4, anti-CD95L and anti-IFN gamma were obtained from Pharmingen (San Diego, Calif.).

Generation of Anti-CCR4 Monoclonal Antibodies, Immunofluorescent Staining, and FACS® Analysis mAbs reactive with CCR4 were generated by immunizing mice with L1.2 cells expressing high levels of transfected CCR4. Six female C57BL6 mice were immunized with $10^7$ cells, intra-peritoneally, 8–12 times at 2 week intervals, and six fusions were performed in an attempt to identify CCR4-specific mAbs. Specifically, four days following an intravenous injection of CCR4/L1.2 cells, the spleen was removed and cells were fused with the SP2/0 cell line as described (Coligan et al., Current Protocols in Immunology. John Wiley and Sons, New York (1992)). Generally 3000–5000 hybridomas were screened per fusion. In one of the six fusions, an anti-CCR4 mAb was detected; this mAb was named 1G1 (IgG1). In an additional seven fusions, a second anti-CCR4 mAb was detected; this mAb was called 2B10 (IgG2a). The 1G1 and 2B10 hybridomas can be cultivated in DMEM, 10% fetal bovine serum, 2 mM glutamine, 1 mM sodium pyruvate and 100 ng/ml IL-6.

1G1 and 2B10 were screened for reactivity to numerous L1.2 transfectants expressing chemokine receptors or orphan G-protein-coupled receptors. PE-conjugated mAbs to CD4, CD8, CD14, CD20, CD25, CD26, CD69, CD45RO, and CD45RA were obtained from Becton Dickinson (San Jose, Calif.). Similar mAbs, as well as anti-CD95 PE, anti-CD3 Cy-Chrome, and anti-CD4 Cy-Chrome were supplied by Pharmingen (La Jolla, Calif.).

To assess reactivity of mAbs against transfected cells or leukocytes, indirect immunofluorescence and flow cytometry were used. Cells were washed once with PBS, and resuspended in 100 μl PBS containing 5% human serum and 0.1% sodium azide (staining buffer), 5 μg/ml purified antibody, 5 μg/ml IgG1 isotype matched control mAb MOPC21 (Sigma Chemical Co., St. Louis, Mo.) or 50 ml hybridoma culture supernatant. After 20 minutes at 4° C., cells were washed twice with staining buffer, and resuspended in 50 ml FITC-conjugated affinity purified F(ab')2 goat anti-mouse IgG (Jackson ImmunoResearch Laboratories, West Grove, Pa.). After incubating for 20 minutes at 4° C., cells were washed once in staining buffer and analyzed on the FACScan® to determine the level of surface expression.

Tissues and Immunohistochemistry

Normal human mediastinal lymph node was obtained from the National Disease Research Interchange (NDRI, Philadelphia, Pa.). Immunohistochemical analysis for CCR4 was performed on frozen tissue samples using techniques previously described (Silber et al., *Lab. Invest.* 70:163 (1994)). The anti-CCR4 mAb 1G1 (10 µg/ml in 0.3% Tritonx100/0.2% Tween 20/1% FCS/5% human AB serum, 0.1% sodium azide) was applied to tissue sections which were incubated overnight at 4° C. An isotype-matched irrelevant mAb (MOPC21; Sigma, St. Louis Mo.) was used at the same concentration as a negative control on step sections of mediastinal node. Subsequently, biotinylated goat anti-mouse IgG and avidin-biotin-alkaline phosphatase complexes (Biogenex, San Ramon, Calif.) were added in sequence. Fast Red (Biogenex, San Ramon, Calif.), containing levamisol to block endogenous alkaline phosphatase activity, was used as the chromogen, and Mayers hematoxylin was used as the counterstain.

Figure 5:
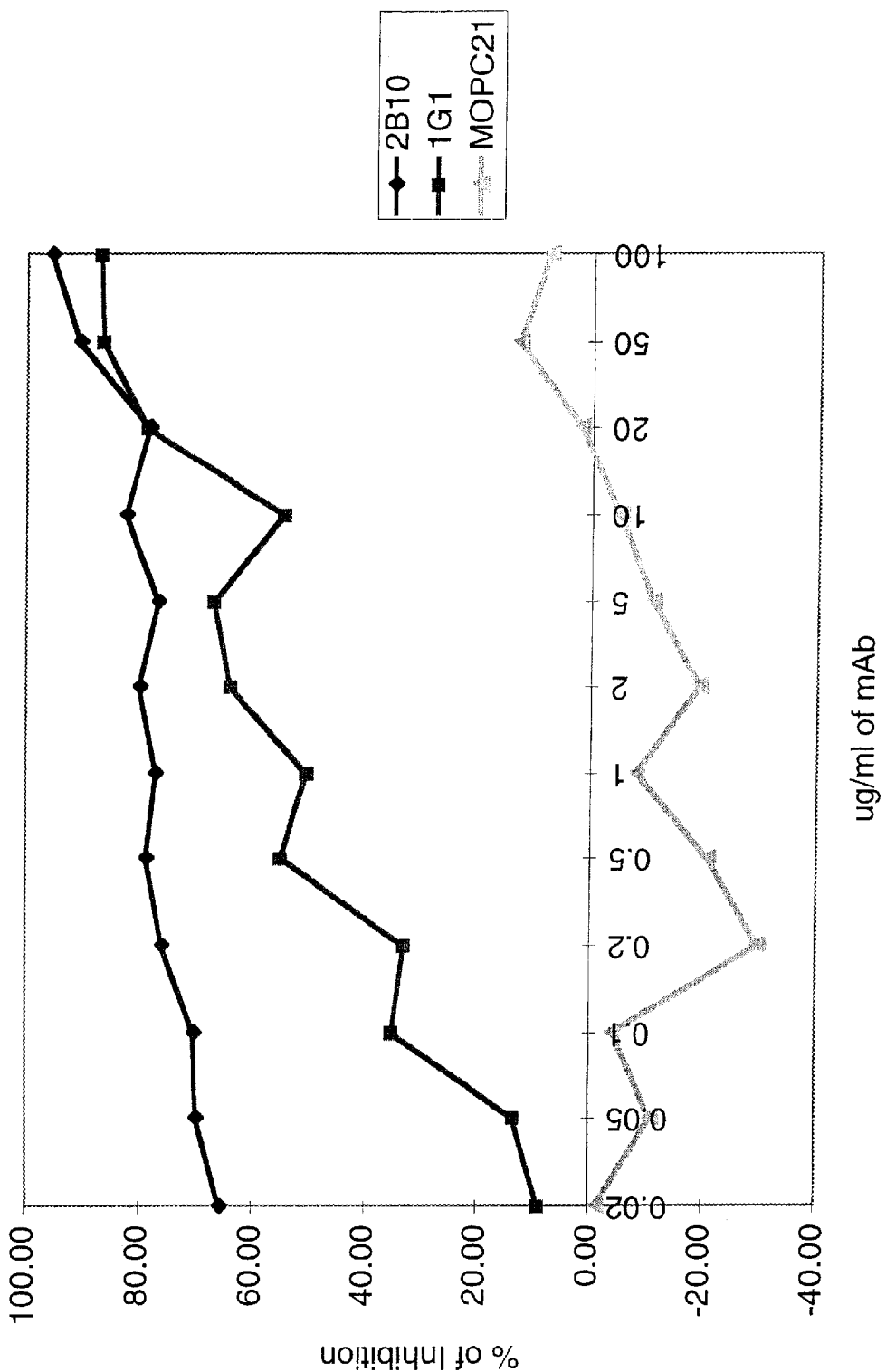
FIG. 5 is a graph showing that mAbs 1G1 and 2B10 inhibit the binding of $^{125}$I-TARC to CCR4/L1.2 transfectants. CCR4/L1.2 cells were incubated with 0.1 nM $^{125}$I-TARC in the absence (total binding) or presence (competitive binding) of a dose range of either mAb 1G1, mAb 2B10, or MOPC21, an IgG1 isotype control. After 60 mintes, excess antibody and chemokine were washed away and reactions were counted. Data shown is the % inhibition of total binding.
Figure 6A:
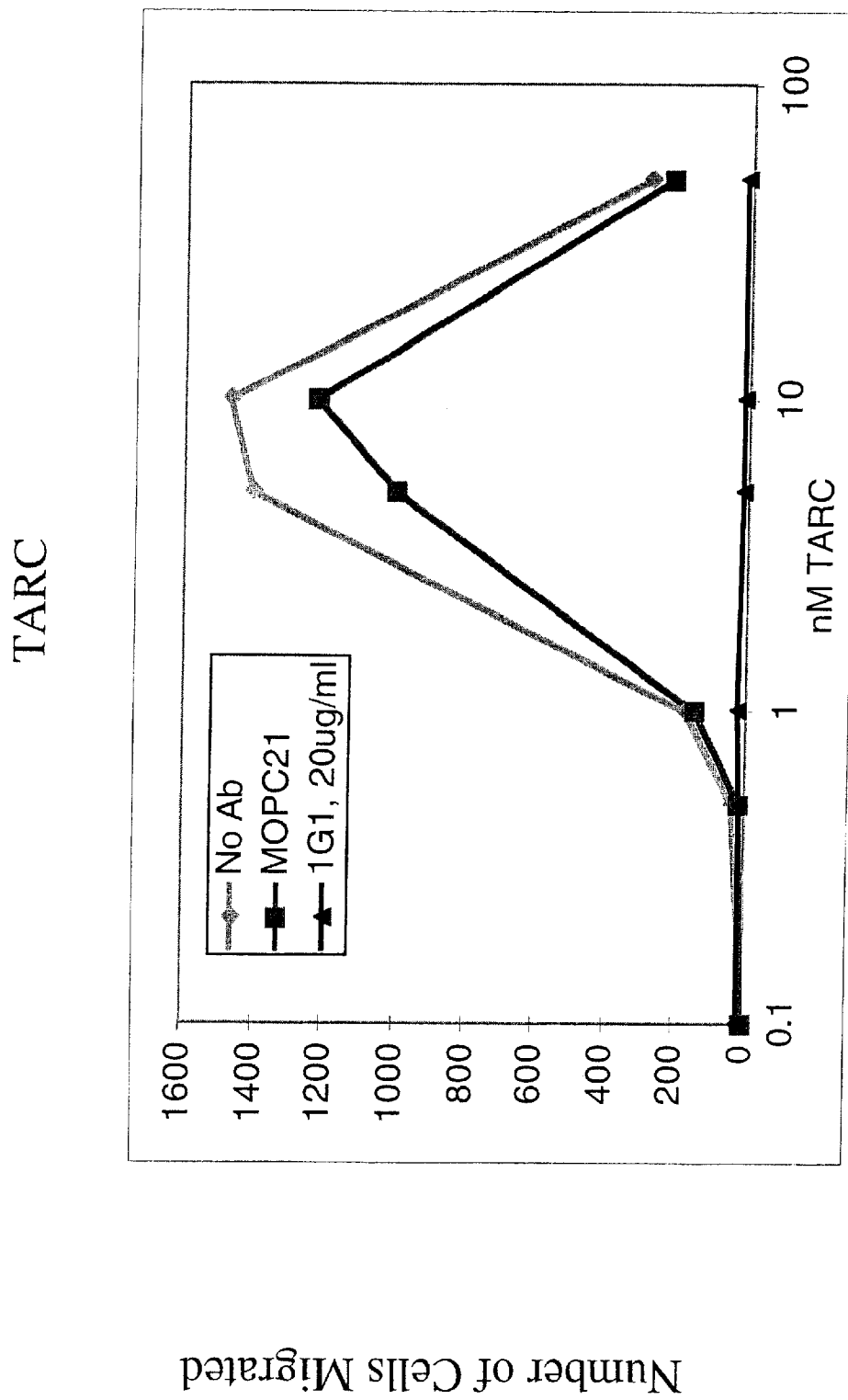
FIGS. 6A–6D are graphs showing inhibition of CCR4/L.12 chemotaxis to TARC and MDC by mAb 1G1. CCR4/L1.2 cells were allowed to chemotax to TARC or MDC in the presence or absence of mAb 1G1 or mAb MOPC21 (the isotype control) in a transwell chemotaxis assay.
Figure 6B:
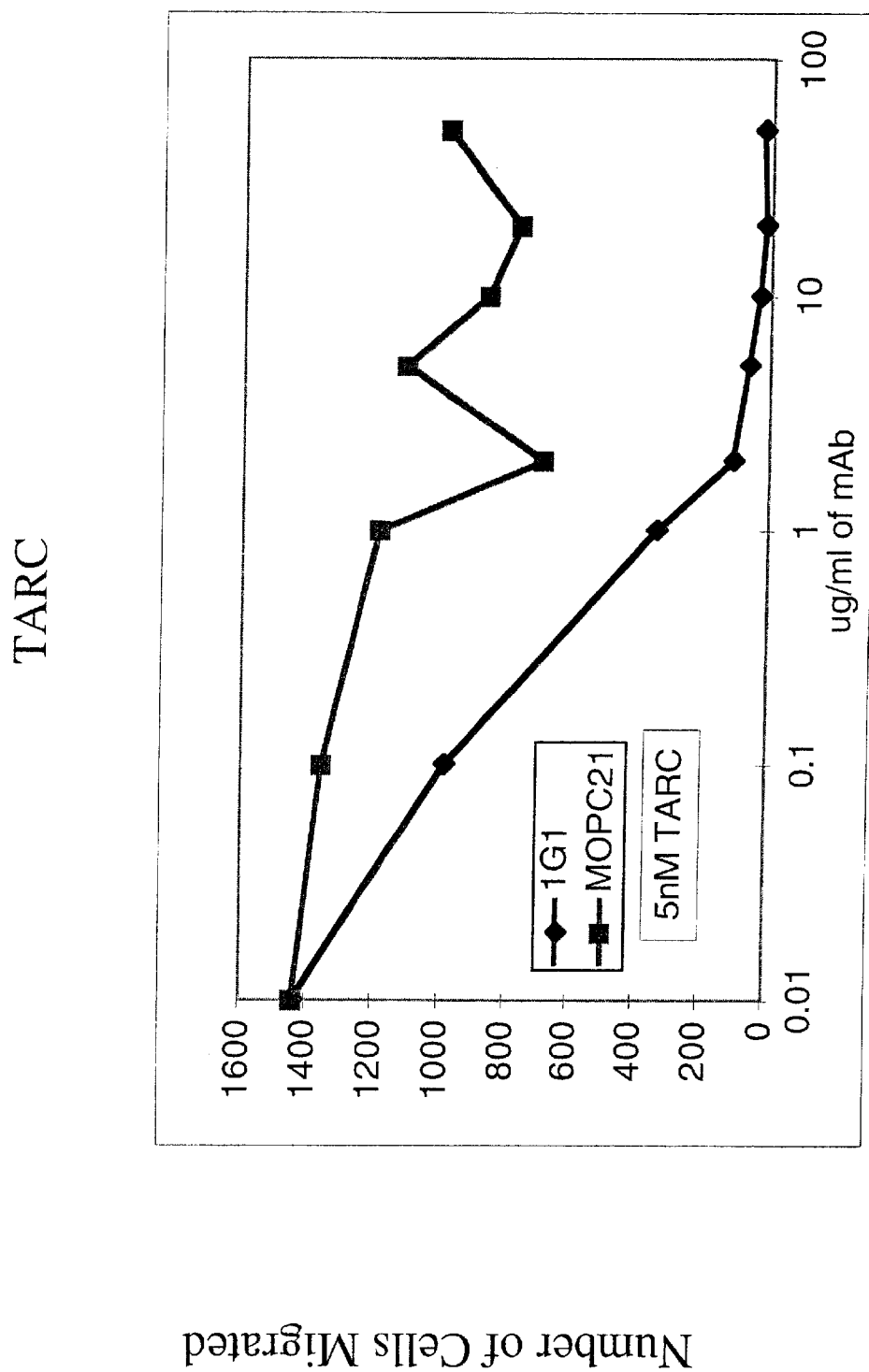
Figure 6C:
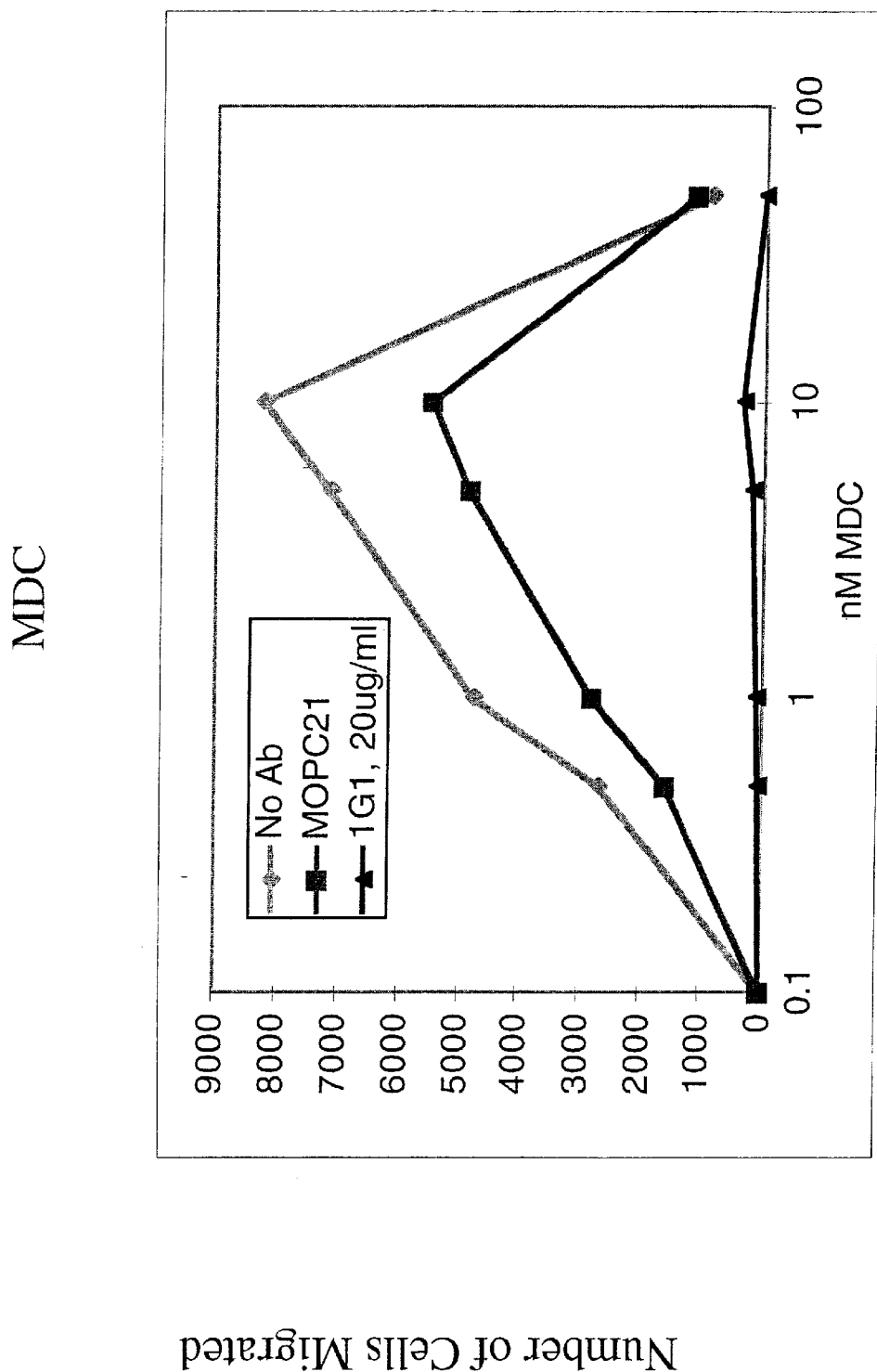
Figure 6D:
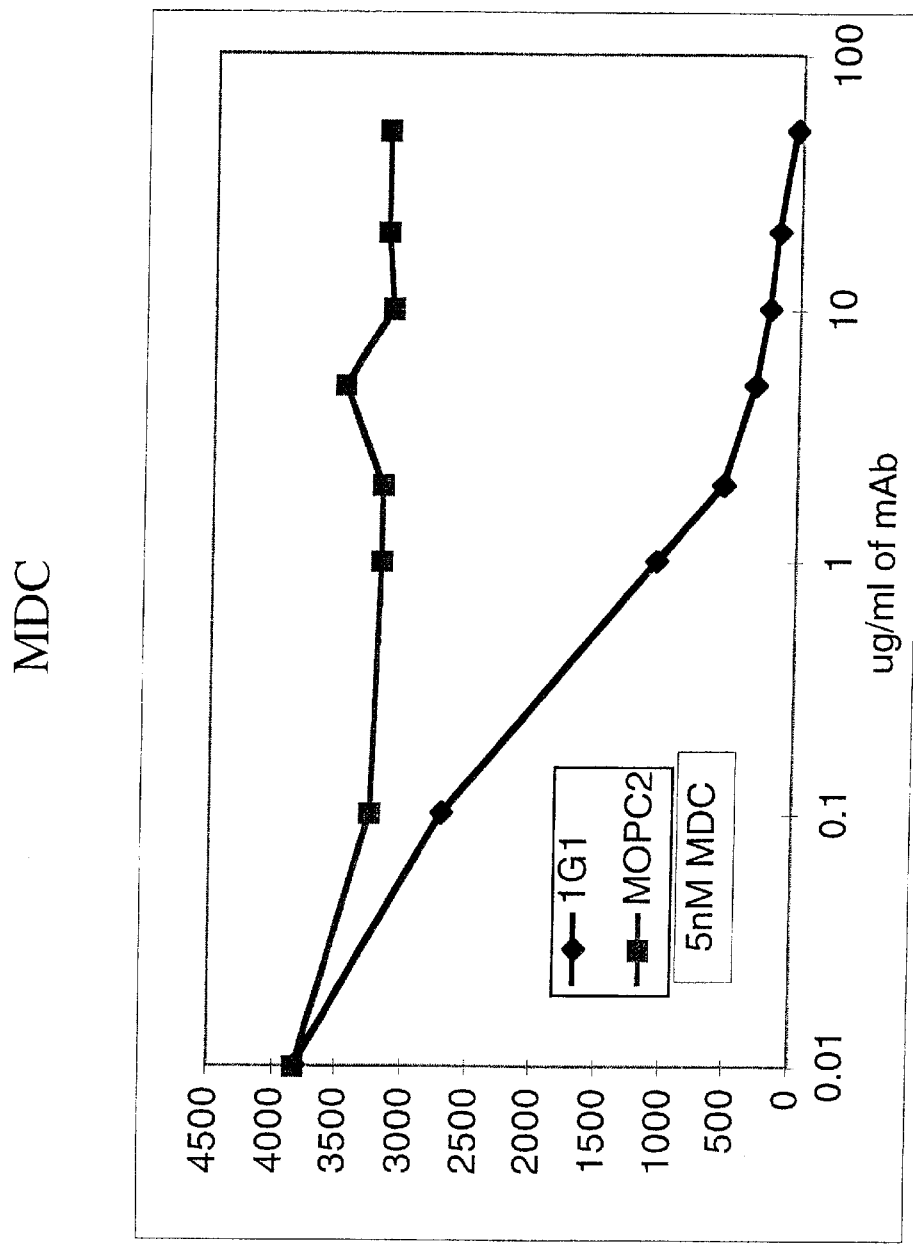
Figure 7A:
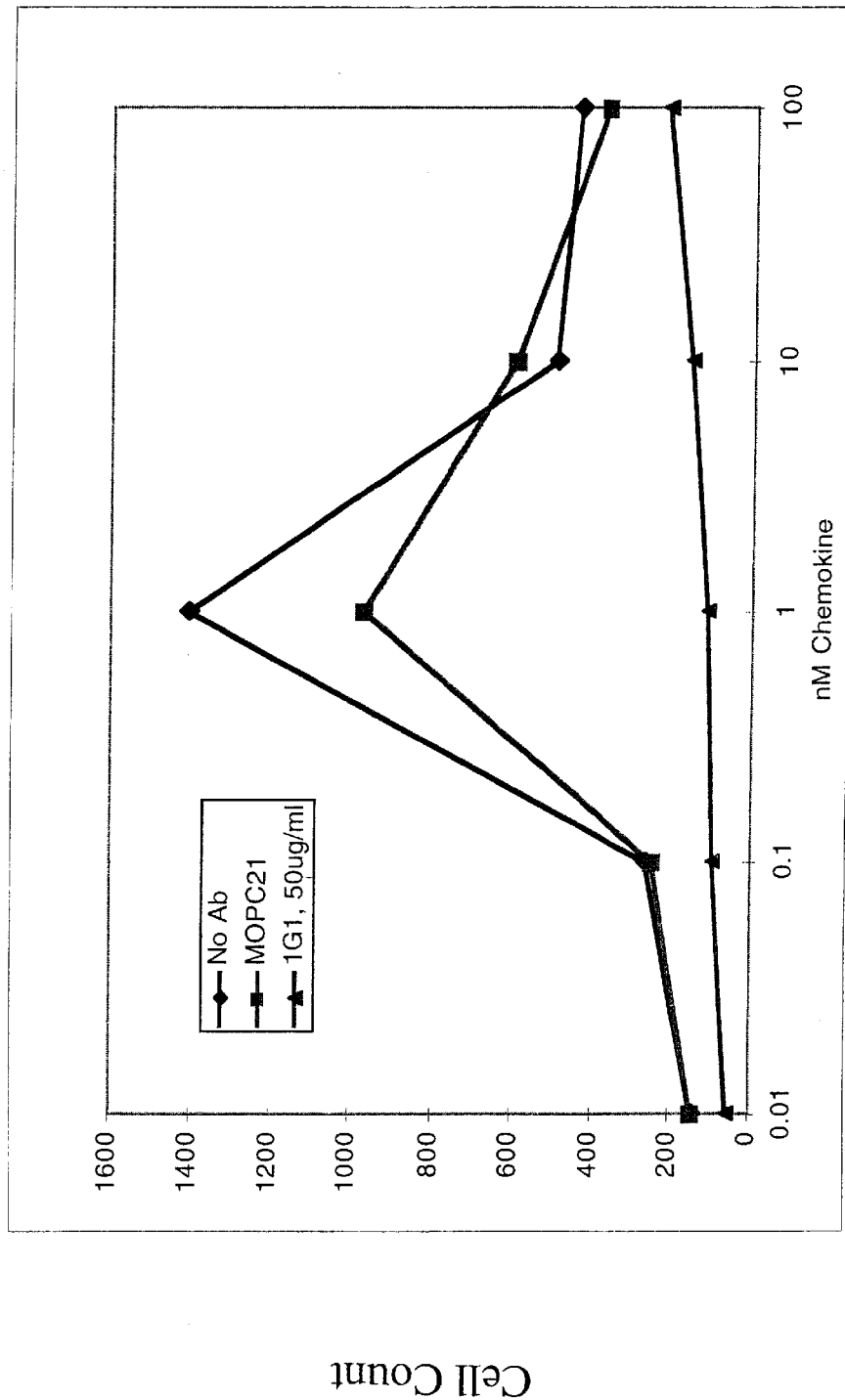
FIGS. 7A–7B are graphs showing inhibition of Peer cell (a human delta-gamma T cell receptor line) chemotaxis to TARC (FIG. 7A) and MDC (FIG. 7B) by mAb 1G1. Peer cells were allowed to chemotax to TARC or MDC in the presence or absence of mAb 1G1 in a transwell chemotaxis assay. A range of concentration of TARC or MDC was used, with 50 ug/ml of anti-CCR4 mAb 1G1 and mAb MOPC21 (isotype control). The number of migrated cells was counted by flow cytometry using forward and side scatter.
Figure 7B:
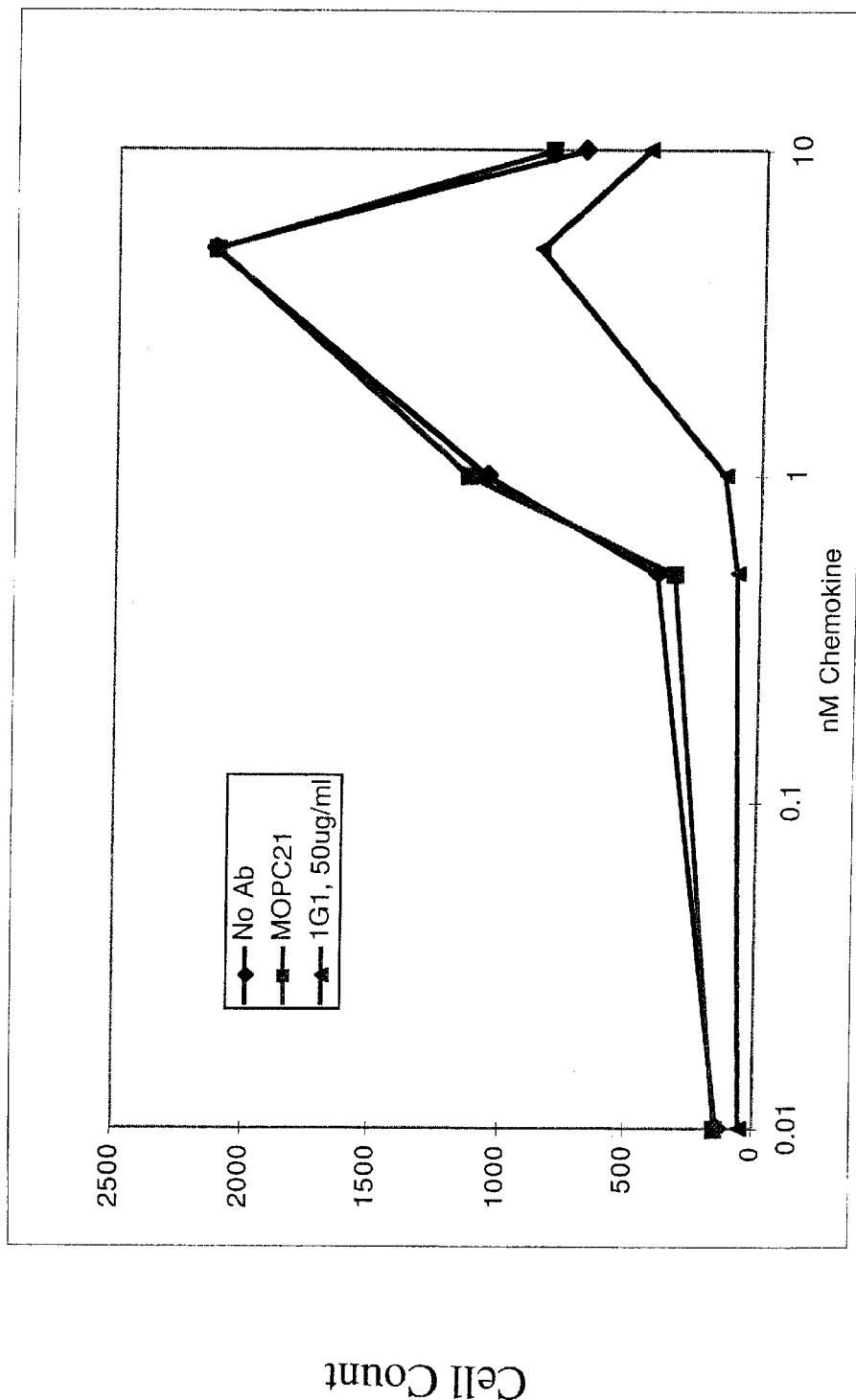
Figure 8:
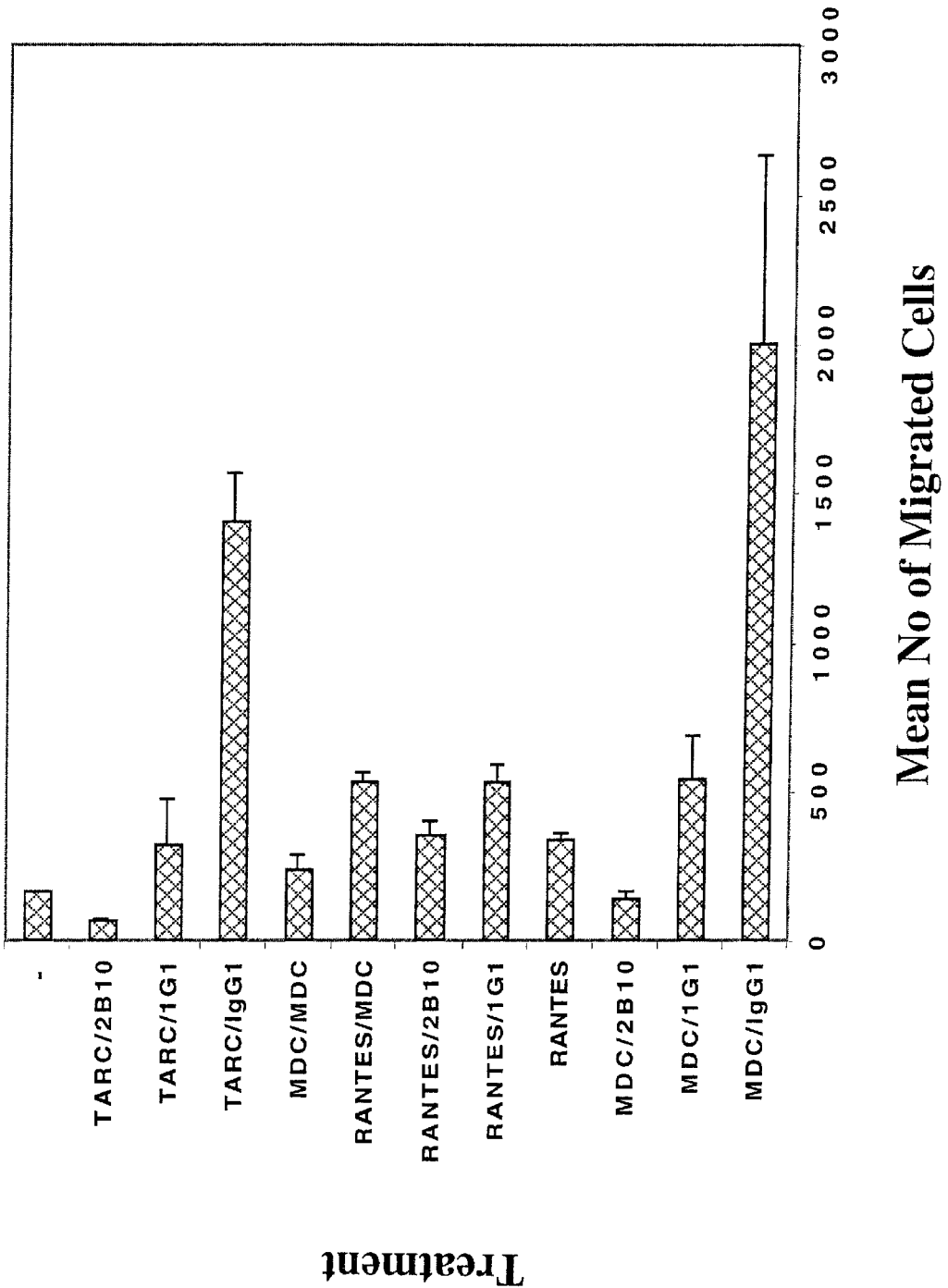
FIG. 8 shows the effect of anti-CCR4 mAbs 1G1 and 2B10 on Th2 migration. Chronically activated Th1/Th2 were generated by two cycles of activation from umbilical CD4 lymphocytes and were pre-incubated with 50 $\mu$g/ml of a IgG1 control mAb, anti-CCR4 mAb 1G1 or anti-CCR4 mAb 2B10. After 10 minutes on ice the Th2 cells were then allowed to migrate for two hours to 100 ng/ml of MDC, TARC, or RANTES. In one case the MDC was pre-incubated with a rabbit polyclonal to MDC for 10 minutes before use (MDC/-MDC). To establish the background migration no chemokine was used in the lower well (−). After this time the cells accumulated in the lower well were counted using a FACSCAN.
Figure 9:
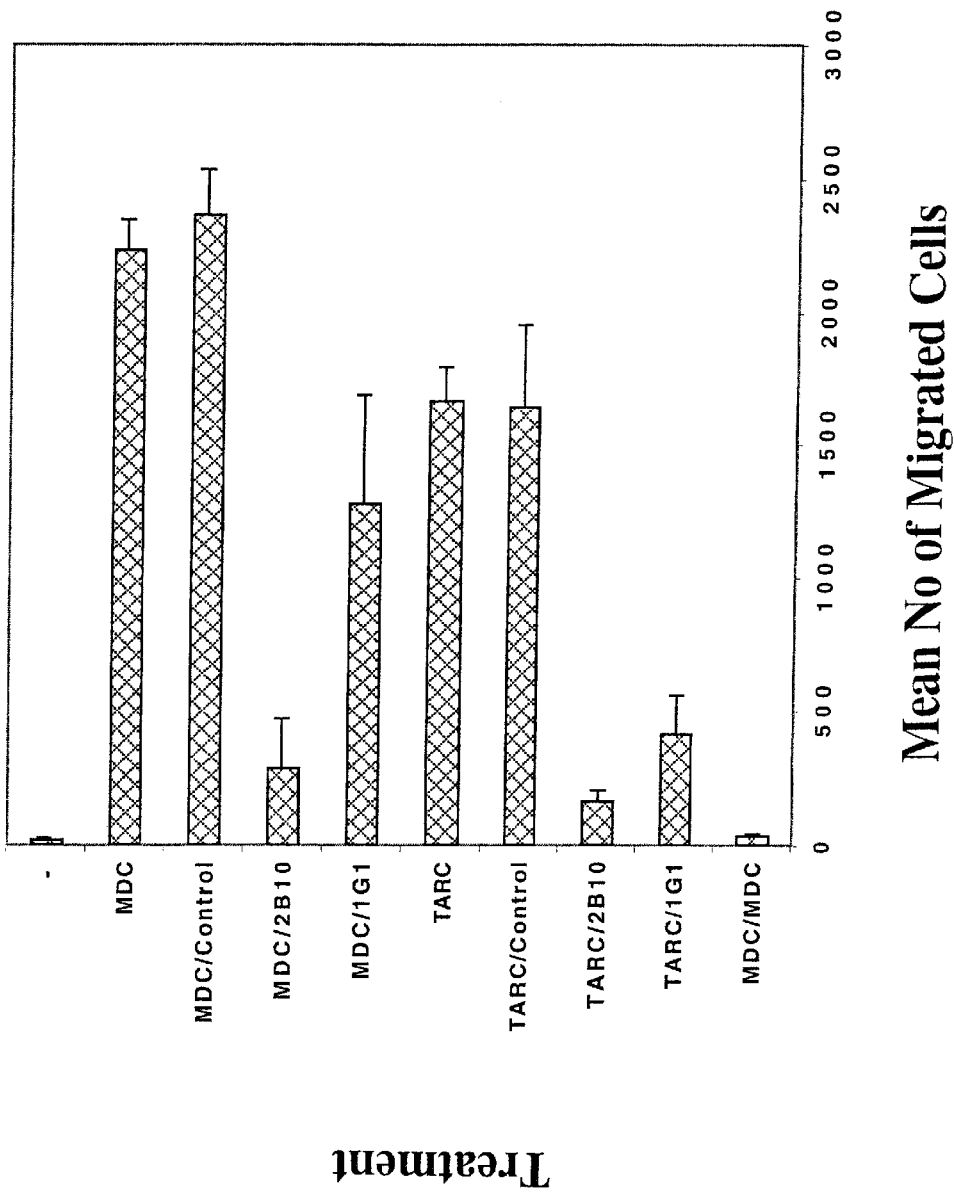
FIG. 9 shows the effect of anti-CCR4 mAbs 1G1 and 2B10 on 24 hour-old CD4 lymphocyte migration. Twenty-four hour-old CD4 lymphocytes were pre-incubated with 50 $\mu$g/ml of a control mAb, anti-CCR4 mAb 1G1 or anti-CCR4 mAb 2B10. After 10 minutes on ice the CD4 lymphocytes were then allowed to migrate for two hours to 100 ng/ml of MDC, TARC, or RANTES. In one case, the MDC was pre-incubated with a rabbit polyclonal to MDC for 10 minutes before use (MDC/-MDC). To establish the background migration, no chemokine was used in the lower well (−). After this time, the cells accumulated in the lower well were counted using a FACSCAN.

$^{125}$I-TARC Binding $^{125}$I-labeled human TARC was purchased from DuPont NEN (Boston, Mass.), and unlabeled chemokines were from Peprotech (Rocky Hill, N.J.) or R&D systems (Minneapolis, Minn.). Chemokine binding to target cells was carried out using the following procedure: CCR4/L1.2 cells were washed and resuspended in binding buffer (50 mM HEPES, pH7.5, 1 mM $CaCl_2$, 5 mM $MgCl_2$, and 0.5% BSA) at $10^7$/ml. For each binding reaction (in a final volume of 100 µl), 25 µl of cell suspension ($2.5 \times 10^5$ cells) was mixed with 0.1 nM radio-labeled chemokine with or without an appropriate amount of anti-CCR4 mAb, or an isotype-matched control mAb. Total binding was determined in the presence of radio-labeled chemokines only, and non-specific binding (background) was determined in the presence of 100 nM unlabeled chemokines. The reactions were incubated at room temperature for 45–60 minutes, and stopped by transferring the mixture to GFB filter plates which were then washed 2–3 times with binding buffer containing 0.5 M NaCl. The plates were dried and MicroScint scintillation fluid was added before counting. Each sample was assayed in duplicate. Results are shown in FIG. 5. The $IC_{50}$ value for 2B10 was approximately 1 ng/ml, and the IC50 for 1G1 was approximately 1 µg/ml (Kaleidagraph software).

Chemotaxis Assays

Chemotaxis with CCR4/L1.2 transfectant cells and Peer cell line were carried out as described previously (Wu et al, *J. Biol. Chem.* 271:31202 (1996); Wu et al., *J. Exp. Med.* 186:1373 (1997)). Briefly, 3 µM pore diameter Transwell inserts from Costar (Costar, Mass.) were used. Chemokine was added at 100 ng/ml in 0.5 ml of RPMI, 0.5% BSA, 10 mM Hepes to the lower well. The cells under study were washed once in RPMI and re-suspended at $4 \times 10^6$ cells/ml in RPMI, 0.5% BSA and 10 mM Hepes. In some cases mAbs were added to 50 µg/ml to the cell suspension and allowed to bind for 10 minutes at 4° C. An aliquot of 200 µl of cell suspension (input of $2 \times 10^6$ cells) was added to each insert. After 2 to 4 hours at 3° C. in a 5% $CO_2$ incubator, the inserts were removed from the plates. Cells migrating to the bottom chamber of the Transwell were enumerated using the FACScan®, by counting cells for 30 seconds. Forward angle and side scatter gates were set to exclude debris or irrelevant cells. The $IC_{50}$ value for 1G1 inhibiton of chemotaxis to MDC and TARC is approximately 0.25 µg/ml.

Results

Figure 4:
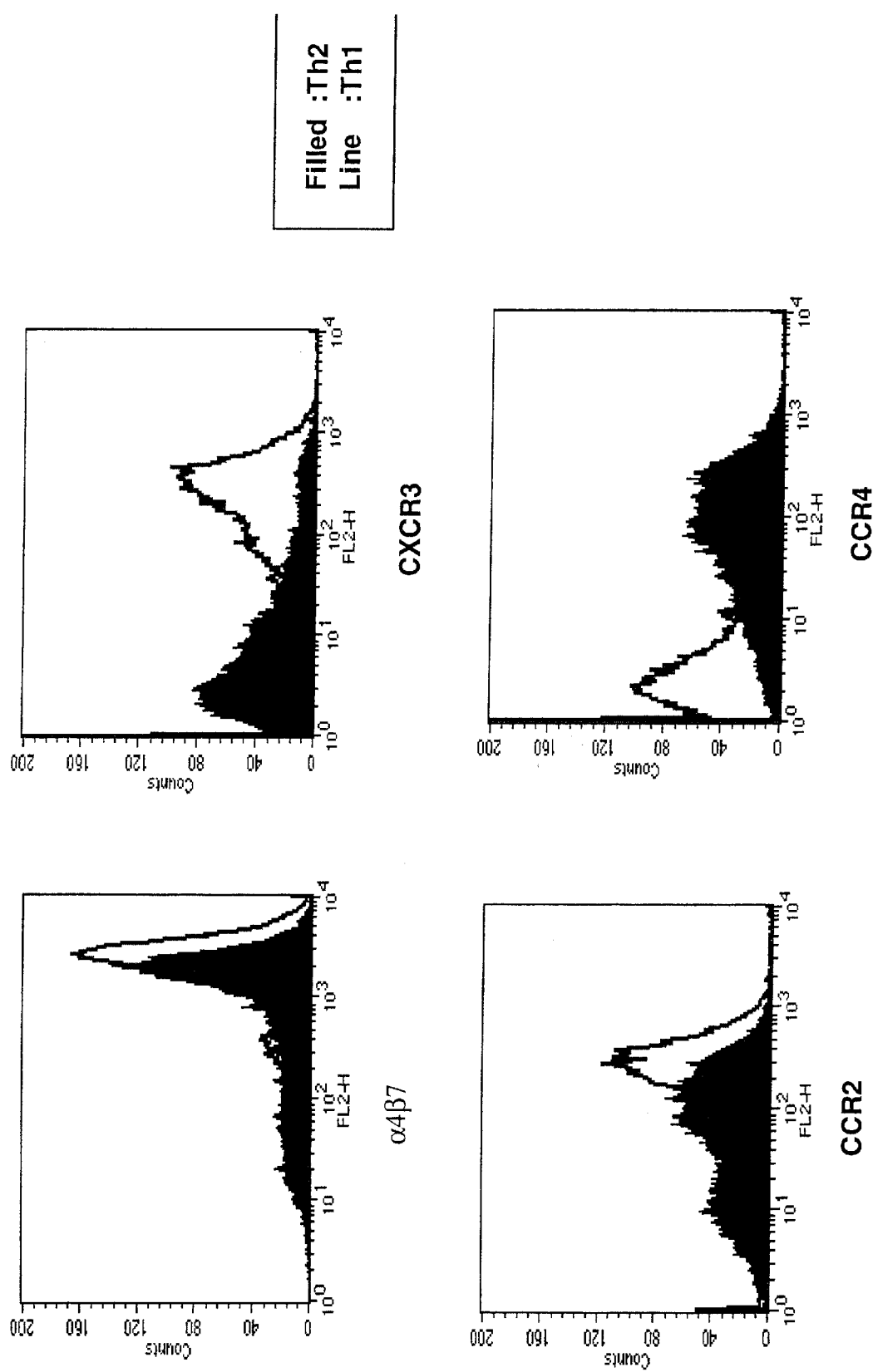
FIG. 4 is a FACScan® profile showing expression of CCR4 on Th2 cells. Chronically activated Th1 (line) and Th2 (filled profile) lymphocytes generated by two cycles of activation from umbilical CD4 lymphocytes were stained with anti-$\alpha 4\beta 7$ mAb Act 1 as a positive control, as this integrin is expressed on both Th1 and Th2 lymphocytes. Staining with anti-CCR2 mAb 1D9 showed that both Th1 and Th2 mAbs express CCR2 while staining with anti-CXCR3 mnAb (R and D, Minneapolis, Minn.) showed that CXCR3 was expressed selectively on in vitro-derived Th1 cells. Using 1G1, CCR4 was found to be expressed selectively on Th2 lymphocytes.

CCR4 is a chemokine receptor expressed on T cells that can be specifically activated by TARC and MDC. To further investigate the expression and functions of CCR4, two monoclonal antibodies, 1G1 and 2B10, were generated against the human CCR4 receptor. Monoclonal antibody 1G1 stains CCR4/L1.2 transfectants but not a panel of over 20 different L1.2 transfectants expressing other chemokine receptors or orphan G protein-coupled receptors (FIG. 1). Monoclonal antibody 2B10 reacts with L1.2 CCR4 transfectants but not with two other chemokine receptor transfectants tested so far. Monoclonal antibody (mAb) 1G1 stains ~15% of the CD4+ peripheral blood lymphocytes, but very few CD8+ T lymphocytes (FIGS. 2A–2b and 3A–3D). CCR4 is expressed on a subset of activated memory T cells; it is expressed on most of the CLA+/a4b7− but not the CLA−/a4b7+ cells. More significantly, mAb 1G1 stains specifically in vitro-derived Th2 but not Th1 cells, whereas CXCR3 is expressed on most of the Th1 but not Th2 cells and CCR2 is expressed on both cell types (FIG. 4). In addition, preliminary immunohistochemistry studies indicate that CCR4 can be detected on subsets of T cells, macrophages, and endothelium in human tonsil and several other tissues. The mAb 1G1 inhibits the binding of $^{125}$I-labeled-TARC to CCR4/L1.2 transfectants (FIG. 5), as well as the chemotaxis of these cells to TARC and MDC (FIGS. 6A–6D, 7A–7B, 8, 9 and 10).

Monoclonal antibody 2B10 was found which stained L1.2 CCR4 transfectants but not the L1.2 parental line or two other chemokine receptor transfectants (gpr-9-6 and V28). As seen with 1G1, 2B10 was found to stain a subset of approximately 15% of peripheral CD4 lymphocytes, but very few CD8 lymphocytes. CD19 lymphocytes and NK cells were not stained by 2B10. The CD4 lymphocytes which were stained by 2B10 were a subset of memory CD4 lymphocytes as defined by expression of CD45RO. As seen with 1G1, 2B10 was found to selectively react with in vitro derived Th2 lymphocytes but not with in vitro derived Th1 lymphocytes. In chemotaxis assays, 2B10 significantly blocked the chemotaxis of peripheral blood CD4 lymphocytes and in vitro derived Th2 lymphocytes to MDC and TARC. These combined results suggest that CCR4 and its ligands may play an important role in Th2 cell-mediated inflammatory responses and in skin, but not mucosal, homing of T lymphocytes.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. An antibody or antigen-binding fragment thereof which binds to a human CC-chemokine receptor 4 (CCR4) or portion of said receptor, wherein said antibody or antigen-binding fragment thereof inhibits binding of a ligand to the receptor, and wherein said antibody or antigen-binding fragment thereof inhibits one or more functions associated with binding of the ligand to the receptor, and wherein said antibody or antigen-binding fragment is selected from the group consisting of:
  a) monoclonal antibody 1G1;
  b) an antibody which can compete with monoclonal antibody 1G1 for binding to human CC-chemokine receptor 4 (CCR4);
  c) monoclonal antibody 2B10;
  d) an antibody which can compete with monoclonal antibody 2B10 for binding to human CC-chemokine receptor 4 (CCR4); and
  e) an antigen-binding fragment of any one of a) through d) which binds to human CC-chemokine receptor 4 (CCR4) or a portion thereof.

2. The 1G1 hybridoma cell line deposited under ATCC Accession No. HB-12624.

3. The 2B10 hybridoma cell line deposited under ATCC Accession No. HB-12625.

4. A monoclonal antibody produced by the hybridoma cell line deposited under ATCC Accession No. HB-12624 or an antigen-binding fragment of said antibody.

5. A monoclonal antibody produced by the hybridoma cell line deposited under ATCC Accession No. HB-12625 or an antigen-binding fragment of said antibody.

6. A humanized antibody or antigen-binding fragment thereof which binds to a human CC-chemokine receptor 4 (CCR4) or portion of said receptor, wherein said humanized antibody comprises one or more antigen-binding regions of monoclonal antibody 1G1 and a portion of an immunoglobulin of human origin.

7. A humanized antibody or antigen-binding fragment thereof which binds to a human CC-chemokine receptor 4 (CCR4) or portion of said receptor, wherein said humanized antibody comprises one or more antigen-binding regions of monoclonal antibody 2B10 and a portion of an immunoglobulin of human origin.

8. A composition comprising an antibody or antigen-binding fragment thereof which binds to a human CC-chemokine receptor 4 (CCR4) or portion of said receptor, wherein said antibody or antigen-binding fragment there of inhibits binding of a ligand to the receptor, and wherein said antibody or antigen-binding fragment thereof inhibits one or more functions associated with binding of the ligand to the receptor, and wherein said antibody or antigen-binding fragment is selected from the group consisting of:
  a) monoclonal antibody 1G1;
  b) an antibody which can compete with monoclonal antibody 1G1 for binding to human CC-chemokine receptor 4 (CCR4);
  c) monoclonal antibody 2B10;
  d) an antibody which can compete with monoclonal antibody 2B10 for binding to human CC-chemokine receptor 4 (CCR4); and
  e) an antigen-binding fragment of any one of a) through d) which binds to human CC-chemokine receptor 4 (CCR4) or a portion thereof,
and an optional physiologically acceptable vehicle.

9. A composition comprising a humanized 1G1 antibody or antigen-binding fragment thereof which binds to a human CC-chemokine receptor 4 (CCR4) or portion of said receptor.

10. A composition comprising a humanized 2B10 antibody or antigen-binding fragment thereof which binds to a human CC-chemokine receptor 4 (CCR4) or portion of said receptor.

11. An antibody or antigen-binding fragment thereof which binds to a mammalian CC-chemokine receptor 4 (CCR4) or portion of said receptor, wherein said antibody or antigen-binding fragment thereof inhibits binding of a ligand to the receptor, and wherein said antibody or antigen-binding fragment thereof inhibits one or more functions associated with binding of the ligand to the receptor, and wherein said antibody or antigen-binding fragment is selected from the group consisting of:

a) monoclonal antibody 1G1;
b) an antibody which can compete with monoclonal antibody 1G1 for binding to mammalian CC-chemokine receptor 4 (CCR4);
c) monoclonal antibody 2B10;
d) an antibody which can compete with monoclonal antibody 2B10 for binding to mammalian CC-chemokine receptor 4 (CCR4); and
e) an antigen-binding fragment of any one of a) through d) which binds to mammalian CC-chemokine receptor 4 (CCR4) or a portion thereof.

12. An antibody or antigen-binding fragment thereof according to claim 11, wherein the ligand is a chemokine.

13. An antibody or antigen-binding fragment thereof according to claim 12, wherein the chemokine is selected from the group consisting of TARC, MDC, and combinations thereof.

14. An antibody or antigen-binding fragment according to claim 11, wherein said antibody is b) or d) and wherein said antibody is a monoclonal antibody.

15. An antibody or antigen-binding fragment according to claim 11, wherein said antibody is b) or d) and said antibody is a chimeric antibody.

16. An antibody or antigen-binding fragment according to claim 11, wherein said antibody is b) or d) and said antibody is a human antibody.

17. An antibody or antigen-binding fragment according to claim 11, wherein said antibody is b) or d) and said antibody is a humanized antibody.

18. An antibody or antigen-binding fragment according to claim 11, wherein said antigen-binding fragment is selected from the group consisting of an Fv fragment, an Fab fragment, an Fab' fragment and an F(ab')$_2$ fragment.

19. An antibody or antigen-binding fragment thereof according to claim 11, wherein said one or more functions associated with binding of the ligand to the receptor are selected from the group consisting of:
a) signaling activity; and
b) stimulation of at least one cellular response.

20. An antibody or antigen-binding fragment thereof according to claim 19, wherein said function is signaling activity and wherein said signaling activity is selected from the group consisting of:
a) activation of a G protein; and
b) induction of an increase in the concentration of cytosolic free calcium.

21. An antibody or antigen-binding fragment thereof according to claim 19, wherein the ligand is a chemokine.

22. An antibody or antigen-binding fragment thereof according to claim 21, wherein the chemokine is selected from the group consisting of TARC, MDC, and combinations thereof.

23. An antibody or antigen-binding fragment thereof according to claim 17, wherein the function is stimulation of at least one cellular response and wherein said cellular response is selected from the group consisting of:
a) stimulation of chemotaxis;
b) exocytosis;
c) release of at least one inflammatory mediator;
d) activation of an integrin; and
e) T cell activation.

24. An antibody or antigen-binding fragment thereof according to claim 23, wherein said antibody or antigen-binding fragment thereof inhibits chemotaxis at a concentration of less than 0.50 µg/ml.

25. An antibody or antigen-binding fragment thereof according to claim 23, wherein said antibody or antigen-binding fragment thereof inhibits chemotaxis at a concentration of less than 0.30 µg/ml.

26. An antibody or antigen-binding fragment thereof according to claim 23, wherein said antibody or antigen-binding fragment thereof inhibits chemotaxis at a concentration of less than 0.27 µg/ml.

27. An antibody or antigen-binding fragment thereof which binds to a human CC-chemokine receptor 4 (CCR4) or portion of said receptor, wherein said antibody or antigen-binding fragment thereof inhibits binding of a ligand to the receptor, and wherein said antibody or antigen-binding fragment thereof inhibits one or more functions associated with binding of the ligand to the receptor, wherein said one or more functions associated with binding of the ligand to the receptor are selected from the group consisting of:
a) signaling activity and
b) stimulation of at least one cellular response, and wherein said antibody or antigen-binding fragment is selected from the group consisting of:
a) monoclonal antibody 1G1;
b) an antibody which can compete with monoclonal antibody 1G1 for binding to human CC-chemokine receptor 4 (CCR4);
c) monoclonal antibody 2B10;
d) an antibody which can compete with monoclonal antibody 2B10 for binding to human CC-chemokine receptor 4 (CCR4); and
e) an antigen-binding fragment of any one of a) through d) which binds to human CC-chemokine receptor 4 (CCR4) or a portion thereof.

28. An antibody or antigen-binding fragment thereof according to claim 27, wherein the function is signaling activity and said signaling activity is selected from the group consisting of
a) activation of a G protein; and
b) induction of an increase in the concentration of cytosolic free calcium.

29. An antibody or antigen-binding fragment thereof according to claim 27, wherein the function is stimulation of at least one cellular response and wherein said cellular response is selected from the group consisting of:
a) stimulation of chemotaxis;
b) exocytosis;
c) release of at least one inflammatory mediator;
d) activation of an integrin; and
e) T cell activation.

30. An antibody or antigen-binding fragment thereof according to claim 29, wherein said antibody or antigen-binding fragment thereof inhibits chemotaxis at a concentration of less than 0.50 µg/ml.

31. An antibody or antigen-binding fragment thereof according to claim 29, wherein said antibody or antigen-binding fragment thereof inhibits chemotaxis at a concentration of less than 0.30 µg/ml.

32. An antibody or antigen-binding fragment thereof according to claim 29, wherein said antibody or antigen-binding fragment thereof inhibits chemotaxis at a concentration of less than 0.27 µg/ml.

33. An antibody or antigen-binding fragment thereof according to claim 27, wherein the ligand is a chemokine.

34. An antibody or antigen-binding fragment thereof according to claim 33, wherein the chemokine is selected from the group consisting of TARC, MDC, and combinations thereof.

35. An antibody or antigen-binding fragment according to claim 19 or claim 27 wherein said antibody is b) or d) and said antibody is a monoclonal antibody.

36. An antibody or antigen-binding fragment according to claim 19 or claim 27, wherein said antibody is b) or d) and said antibody is a chimeric antibody.

37. An antibody or antigen-binding fragment according to claim 19 or claim 27, wherein said antibody is b) or d) and said antibody is a human antibody.

38. An antibody or antigen-binding fragment according to claim 19 or claim 27, wherein said antibody is b) or d) and said antibody is a humanized antibody.

39. An antibody or antigen-binding fragment according to claim 19 or claim 27, wherein said antigen-binding fragment is selected from the group consisting of an Fv fragment, an Fab fragment, an Fab' fragment and an F(ab')$_2$ fragment.

40. A test kit for use in detecting the presence of a mammalian CC-chemokine receptor 4 (CCR4) or portion thereof in a biological sample comprising
    a) at least one antibody or antigen-binding fragment thereof which binds to a mammalian CC-chemokine receptor 4 (CCR4) or portion of said receptor, wherein said antibody or antigen-binding fragment thereof inhibits binding of a ligand to the receptor, and wherein said antibody or antigen-binding fragment thereof inhibits one or more functions associated with binding of the ligand to the receptor, and wherein said antibody or antigen-binding fragment is selected from the group consisting of:
        1) monoclonal antibody 1G1;
        2) an antibody which can compete with monoclonal antibody 1G1 for binding to mammalian CC-chemokine receptor 4 (CCR4);
        3) monoclonal antibody 2B10;
        4) an antibody which can compete with monoclonal antibody 2B10 for binding to mammalian CC-chemokine receptor 4 (CCR4); and
        5) an antigen-binding fragment of any one of 1) through 4) which binds to mammalian CC-chemokine receptor 4 (CCR4) or a portion thereof; and
    b) one or more ancillary reagents suitable for detecting the presence of a complex between said antibody or antigen-binding fragment thereof and said mammalian CC-chemokine receptor 4 (CCR4) or a portion thereof.

41. A test kit according to claim 40, wherein said one or more functions associated with binding of the ligand to the receptor are selected from the group consisting of:
    a) signaling activity; and
    b) stimulation of at least one cellular response.

42. A test kit according to claim 41, wherein the function is signaling activity and said signaling activity is selected from the group consisting of:
    a) activation of a G protein; and
    b) induction of an increase in the concentration of cytosolic free calcium.

43. A test kit according to claim 41, wherein the function is stimulation of at least one cellular response and wherein said cellular response is selected from the group consisting of:
    a) stimulation of chemotaxis;
    b) exocytosis;
    c) release of at least one inflammatory mediator;
    d) activation of an integrin; and
    e) T cell activation.

44. A test kit according to claim 43, wherein said antibody or antigen-binding fragment thereof inhibits chemotaxis at a concentration of less than 0.50 µg/ml.

45. A test kit according to claim 43, wherein said antibody or antigen-binding fragment thereof inhibits chemotaxis at a concentration of less than 0.30 µg/ml.

46. A test kit according to claim 43, wherein said antibody or antigen-binding fragment thereof inhibits chemotaxis at a concentration of less than 0.27 µg/ml.

47. A composition comprising an antibody or antigen-binding fragment thereof which binds to a mammalian CC-chemokine receptor 4 (CCR4) or portion of said receptor, wherein said antibody or antigen-binding fragment thereof inhibits binding of a ligand to the receptor, and wherein said antibody or antigen-binding fragment thereof inhibits one or more functions associated with binding of the ligand to the receptor, and wherein said antibody or antigen-binding fragment is selected from the group consisting of:
    a) monoclonal antibody 1G1;
    b) an antibody which can compete with monoclonal antibody 1G1 for binding to mammalian CC-chemokine receptor 4 (CCR4);
    c) monoclonal antibody 2B10;
    d) an antibody which can compete with monoclonal antibody 2B10 for binding to mammalian CC-chemokine receptor 4 (CCR4); and
    e) an antigen-binding fragment of any one of a) through d) which binds to mammalian CC-chemokine receptor 4 (CCR4) or a portion thereof,
and an optional physiologically acceptable vehicle.

48. A composition according to claim 47, wherein the ligand is selected from the group consisting of any one or more of TARC, MDC, and combinations thereof.

49. A composition according to claim 47, wherein said one or more functions associated with binding of the ligand to the receptor are selected from the group consisting of:
    a) signaling activity; and
    b) stimulation of at least one cellular response.

50. A composition according to claim 49, wherein the function is signaling activity and said signaling activity is selected from the group consisting of
    a) activation of a G protein; and
    b) induction of an increase in the concentration of cytosolic free calcium.

51. A composition according to claim 49, wherein the ligand is a chemokine.

52. A composition according to claim 51, wherein the chemokine is selected from the group consisting of any one or more of TARC, MDC, and combinations thereof.

53. A composition according to claim 49, wherein the function is stimulation of at least one cellular response and wherein said cellular response is selected from the group consisting of:
    a) stimulation of chemotaxis;
    b) exocytosis;
    c) release of at least one inflammatory mediator;
    d) activation of an integrin; and
    e) T cell activation.

54. A composition according to claim 53, wherein said antibody or antigen-binding fragment thereof inhibits chemotaxis at a concentration of less than 0.50 µg/ml.

55. A composition according to claim 53, wherein said antibody or antigen-binding fragment thereof inhibits chemotaxis at a concentration of less than 0.30 µg/ml.

56. A composition according to claim 53, wherein said antibody or antigen-binding fragment thereof inhibits chemotaxis at a concentration of less than 0.27 µg/ml.

57. A composition comprising an antibody or antigen-binding fragment thereof which binds to a human CC-chemokine receptor 4 (CCR4) or portion of said receptor, wherein said antibody or antigen-binding fragment thereof inhibits binding of a ligand to the receptor, and wherein said antibody or antigen-binding fragment thereof inhibits one or more functions associated with binding of the ligand to the receptor, wherein said one or more functions associated with binding of the ligand to the receptor are selected from the group consisting of:
  a) signaling activity; and
  b) stimulation of at least one cellular response, and wherein said antibody or antigen-binding fragment is selected from the group consisting of:
    a) monoclonal antibody 1G1;
    b) an antibody which can compete with monoclonal antibody 1G1 for binding to human CC-chemokine receptor 4 (CCR4);
    c) monoclonal antibody 2B10;
    d) an antibody which can compete with monoclonal antibody 2B10 for binding to human CC-chemokine receptor 4 (CCR4); and
    e) an antigen-binding fragment of any one of a) through d) which binds to human CC-chemokine receptor 4 (CCR4) or a portion thereof,
and an optional physiologically acceptable vehicle.

58. A composition according to claim 57, wherein the function is signaling activity and the signaling activity is selected from the group consisting of:
  a) activation of a G protein; and
  b) induction of an increase in the concentration of cytosolic free calcium.

59. A composition according to claim 57, wherein the function is stimulation of at least one cellular response and wherein said cellular response is selected from the group consisting of:
  a) stimulation of chemotaxis;
  b) exocytosis;
  c) release of at least one inflammatory mediator;
  d) activation of an integrin; and
  e) T cell activation.

60. A composition according to claim 59, wherein said antibody or antigen-binding fragment thereof inhibits chemotaxis at a concentration of less than 0.50 µg/ml.

61. A composition according to claim 59, wherein said antibody or antigen-binding fragment thereof inhibits chemotaxis at a concentration of less than 0.30 µg/ml.

62. A composition according to claim 59 wherein said antibody or antigen-binding fragment thereof inhibits chemotaxis at a concentration of less than 0.27 µg/ml.

63. A composition according to claim 57, wherein the ligand is a chemokine.

64. A composition according to claim 63, wherein the chemokine is selected from the group consisting of any one or more of TARC, MDC, and combinations thereof.

* * * * *

UNITED STATES PATENT AND TRADEMARK OFFICE
CERTIFICATE OF CORRECTION

PATENT NO.   : 6,448,930 B1
DATED        : September 10, 2002
INVENTOR(S)  : Judd It is certified that error appears in the above-identified patent and that said Letters Patent is hereby corrected as shown below:

Column 1,
Line 40, reads "demands,, as well as" and should read -- demands, as well as --
Line 57, reads "performnance" and should read -- performance --

Column 2,
Line 28, reads "surfaces being" and should read -- surfaces being configured and oriented to achieve substantially 360° coverage by the antenna elements --

Column 5,
Lines 35 and 48, reads "comer" and should read -- corner --
Line 61, reads "oppositely pair of surfaces' and should read -- oppositely facing pair of surfaces --

Column 7,
Line 20, reads "The elements may patches, dipoles," and should read -- The elements may be patches, dipoles, --
Line 28, reads "elements may be as previously as described" and should read -- elements may be as previously described --

Column 9,
Line 21, reads "antenna elements, and, further" and should read -- antenna elements, and further --

Signed and Sealed this

Nineteenth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,488,930 B1
DATED         : December 3, 2002
INVENTOR(S)   : Lijun Wu, Nancy Ruffing and David Andrew It is certified that error appears in the above-identified patent and that said Letters Patent is hereby corrected as shown below:

Column 31,
Line 55, please delete "claim 17" and insert therefor -- claim 19 --.

Signed and Sealed this

Twentieth Day of January, 2004

JON W. DUDAS
*Acting Director of the United States Patent and Trademark Office*

SEQUENCE LISTING

<160> NUMBER OF SEQ ID NOS: 2

<210> SEQ ID NO 1
<211> LENGTH: 34
<212> TYPE: DNA
<213> ORGANISM: Artificial Sequence
<220> FEATURE:
<223> OTHER INFORMATION: oligonucleotide primer

<400> SEQUENCE: 1
ccaaccaagc ttatgaaccc cacggatata gcag        34

<210> SEQ ID NO 2
<211> LENGTH: 38
<212> TYPE: DNA
<213> ORGANISM: Artificial Sequence
<220> FEATURE:
<223> OTHER INFORMATION: oligonucleotide primer

<400> SEQUENCE: 2
ccaacctcta gattagagca tcatggagat catgatcc        38